US008039683B2

(12) United States Patent
Qin et al.

(10) Patent No.: US 8,039,683 B2
(45) Date of Patent: Oct. 18, 2011

(54) ABSORBENT COMPOSITES HAVING IMPROVED FLUID WICKING AND WEB INTEGRITY

(75) Inventors: Jian Qin, Appleton, WI (US); James H. Wiley, Tacoma, WA (US); Paul B. Stevenson, Elma, WA (US); Stanley L. Bryant, Jr., Tacoma, WA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 727 days.

(21) Appl. No.: 11/974,845

(22) Filed: Oct. 15, 2007

(65) Prior Publication Data

US 2009/0099541 A1 Apr. 16, 2009

(51) Int. Cl.
*A61F 13/15* (2006.01)
*A61F 13/20* (2006.01)
(52) U.S. Cl. ........................ 604/368; 604/367
(58) Field of Classification Search .................. 604/367, 604/368; 524/44
See application file for complete search history.

(56) References Cited

U.S. PATENT DOCUMENTS

| | | | |
|---|---|---|---|
| 3,589,364 A | 6/1971 | Dean et al. | |
| 3,731,686 A | 5/1973 | Chatterjee | |
| 3,849,241 A | 11/1974 | Butin et al. | |
| 3,858,585 A | 1/1975 | Chatterjee | |
| 4,076,663 A | 2/1978 | Masuda et al. | |
| 4,100,324 A | 7/1978 | Anderson et al. | |
| 4,169,121 A | 9/1979 | Pietsch et al. | |
| 4,200,557 A | 4/1980 | Chatterjee et al. | |
| 4,250,306 A | 2/1981 | Lask et al. | |
| 4,286,082 A | 8/1981 | Tsubakimoto et al. | |
| 4,579,943 A | 4/1986 | Kamide et al. | |
| 4,587,154 A | 5/1986 | Hotchkiss et al. | |
| 4,604,313 A | 8/1986 | McFarland et al. | |
| 4,655,757 A | 4/1987 | McFarland et al. | |
| 4,666,647 A | 5/1987 | Enloe et al. | |
| 4,724,114 A | 2/1988 | McFarland et al. | |
| 4,761,258 A | 8/1988 | Enloe | |
| 4,927,582 A | 5/1990 | Bryson | |
| 4,940,464 A | 7/1990 | Van Gompel et al. | |
| 5,114,781 A | 5/1992 | Morman | |
| 5,116,662 A | 5/1992 | Morman | |
| 5,173,521 A | 12/1992 | Ishino | |
| 5,350,624 A | 9/1994 | Georger et al. | |
| 5,470,964 A | 11/1995 | Qin | |
| 5,486,166 A | 1/1996 | Bishop et al. | |
| 5,490,846 A | 2/1996 | Ellis et al. | |
| 5,498,705 A | 3/1996 | Oin | |
| 5,550,189 A | 8/1996 | Qin et al. | |
| 5,725,601 A | 3/1998 | Tajiri et al. | |
| 5,731,083 A | 3/1998 | Bahia et al. | |
| 5,766,389 A | 6/1998 | Brandon et al. | |
| 5,820,973 A | 10/1998 | Dodge, II et al. | |
| 5,847,031 A * | 12/1998 | Klimmek et al. | ............ 524/44 |
| 5,883,028 A | 3/1999 | Morman et al. | |
| 5,985,434 A | 11/1999 | Qin et al. | |
| 5,998,511 A | 12/1999 | Westland et al. | |
| 6,075,177 A | 6/2000 | Bahia et al. | |
| 6,330,735 B1 | 12/2001 | Hahn et al. | |
| 6,361,651 B1 | 3/2002 | Sun | |
| 6,362,389 B1 | 3/2002 | McDowall et al. | |
| 6,416,697 B1 | 7/2002 | Venturino et al. | |
| 6,433,058 B1 | 8/2002 | Weir et al. | |
| 6,479,415 B1 | 11/2002 | Erspamer et al. | |
| 6,500,947 B1 | 12/2002 | West et al. | |
| 6,552,245 B1 | 4/2003 | Roessler et al. | |
| 6,583,331 B1 | 6/2003 | McCormack et al. | |
| 6,610,903 B1 | 8/2003 | Latimer et al. | |
| 6,630,088 B1 | 10/2003 | Venturino et al. | |
| 6,641,134 B1 | 11/2003 | Dobbertin et al. | |
| 6,645,190 B1 | 11/2003 | Olson et al. | |
| 6,673,980 B1 | 1/2004 | Varona et al. | |
| 6,710,225 B1 * | 3/2004 | Everett et al. | ............... 604/378 |
| 6,716,929 B2 | 4/2004 | Wilson | |
| 6,844,066 B2 | 1/2005 | Hamed | |
| 6,846,924 B1 | 1/2005 | Malmgren et al. | |
| 6,951,933 B2 | 10/2005 | West et al. | |
| 7,052,775 B2 | 5/2006 | Dohrn et al. | |
| 7,094,318 B2 | 8/2006 | Hamed et al. | |
| 7,230,049 B2 | 6/2007 | Weerawarna | |
| 7,241,836 B2 | 7/2007 | Weerawarna | |

(Continued)

FOREIGN PATENT DOCUMENTS

| | | |
|---|---|---|
| EP | 0 007 134 A1 | 1/1980 |
| EP | 0 699 793 A1 | 3/1996 |
| EP | 1 676 865 A1 | 7/2006 |
| EP | 1 676 866 A1 | 7/2006 |
| EP | 1 373 610 B1 | 6/2007 |

(Continued)

OTHER PUBLICATIONS

American Society for Testing Materials (ASTM) Designation: D1238-70, "Standard Method for Measuring Flow Rates of Thermoplastics by Extrusion Plastometer," pp. 415-426, effective Jun. 1970.
Lawrence, K.D. et al., "An Improved Device for the Formation of Superfine, Thermoplastic Fibers," *NRL Report 5265*, U.S. Naval Research Laboratory, Washington, D.C., Feb. 11, 1959, pp. 1-7.
Neumann, A.W., and R.J. Good, "Techniques of Measuring Contact Angles," Chapter 2, *Surface and Colloid Science—Experimental Methods*, vol. 11, edited by R.J. Good and R.R. Stromberg, Plenum Press, 1979, pp. 31-91.
Wente, V.A. et al., "Manufacture of Superfine Organic Fibers," *NRL Report 4364*, U.S. Naval Research Laboratory, Washington, D.C., May 25, 1954, pp. 1-15.

(Continued)

*Primary Examiner* — Melanie Hand
(74) *Attorney, Agent, or Firm* — Bryan R. Rosiejka; Denise L. Stoker

(57) ABSTRACT

An absorbent article includes an absorbent composite which comprises substantially water-insoluble, water-swellable, non-regenerated, carboxyalkyl cellulose fibers. The fibers have a surface having the appearance of the surface of a cellulose fiber and comprise a plurality of first intra-fiber multi-valent metal ion crosslinks and a plurality of second intra-fiber crosslinks selected from ether crosslinks or ester crosslinks. In addition, the absorbent composite has been subjected to a treatment to create interfiber bonding between the fibers of the composite either throughout the composite or only on the surface of the composite.

11 Claims, 13 Drawing Sheets

U.S. PATENT DOCUMENTS

| | | |
|---|---|---|
| 2003/0125684 A1 | 7/2003 | Qin |
| 2006/0004336 A1 | 1/2006 | Zhang et al. |
| 2006/0137838 A1 * | 6/2006 | Luo et al. ............ 162/9 |
| 2008/0082064 A1 | 4/2008 | Luo et al. |
| 2008/0082068 A1 | 4/2008 | Qin et al. |
| 2008/0082069 A1 | 4/2008 | Qin et al. |
| 2008/0147032 A1 | 6/2008 | Luo et al. |

FOREIGN PATENT DOCUMENTS

| | | |
|---|---|---|
| EP | 1 925 323 A1 | 5/2008 |
| GB | 2 151 272 A | 7/1985 |
| GB | 2 220 881 A | 1/1990 |
| JP | 10-025662 A | 1/1998 |
| WO | WO 00/37009 A2 | 6/2000 |
| WO | WO 2005/037328 A2 | 4/2005 |

* cited by examiner

ABSORBENT COMPOSITES HAVING IMPROVED FLUID WICKING AND WEB INTEGRITY

BACKGROUND

Articles, such as absorbent articles, are useful for absorbing many types of fluids, including fluids secreted or eliminated by the human body. Such articles, such as infant diapers, child training pants and adult incontinence products for example, typically comprise an absorbent composite (often as a component referred to as the "core") which, among other things, performs the function of absorbing and/or retaining fluids which are insulted into an absorbent article. Absorbent composites typically comprise superabsorbent materials in particulate form, as well as cellulose fibers. In general, the superabsorbent material provides fluid absorption capacity while the cellulose fibers function as an aid to enhance fluid wicking and wet integrity, which can allow fuller utilization of the article by allowing fluid to be transported to regions that are away from the point of insult. Thus, while the absorbent composite's liquid retention or storage capacity is due in large part to the superabsorbent particles, the absorbent composite's fibrous matrix provides the essential functions of liquid wicking, intake, distribution, pad strength and integrity, as well as some amount of absorbency under load. These desirable properties are attributable to the fact that the matrix includes cellulosic fibers, typically wood pulp in fiber form, such as cellulose fibers ("fluff"). Cellulose fibers and superabsorbent materials are therefore frequently used in absorbent articles to help improve the absorbent properties of such articles.

There is a continuing effort to improve the performance of such absorbent composites, especially at high levels of fluid saturation, to thereby reduce the occurrence of leakage and to improve fit and comfort. This is particularly significant when such articles are subjected to repeated fluid insults during use. This has become an increasing challenge as recent efforts in absorbent article design have generally focused on using higher concentrations of superabsorbent materials and less fluff to make the absorbent structures thinner and more flexible. However, notwithstanding the increase in total absorbent capacity obtained by increasing the concentration of superabsorbent material, such absorbent articles may still nevertheless leak during use. Such leakage may in part be the result of the absorbent composite component of an absorbent article having an insufficient intake rate (i.e., the rate at which a fluid insult can be taken into and entrained within the absorbent composite for subsequent absorption by the superabsorbent material) due to low permeability and lack of available void volume. Such leakage may in part be the result of the absorbent composite component of an absorbent article having an insufficient utilization efficiency of the entire absorbent composite due to low fluid wicking and low wet integrity.

The inclusion of superabsorbent materials in a fibrous matrix and their incorporation into absorbent composites typically has the effect of reducing an absorbent article's overall bulk while at the same time increasing its liquid absorbent capacity and enhancing skin dryness for the products' wearers. Superabsorbent materials ("superabsorbents") are generally polymer based and may be available in many forms, such as powders, granules, microparticles and films, for example. Upon contact with fluids, such superabsorbents swell by absorbing the fluids into their structures. In general, superabsorbents are water-swellable, generally water-insoluble absorbent materials having a liquid absorbent capacity of at least about 10, preferably of about 20, and often up to about 100 times their weight in saline or more. In general, superabsorbent materials can quickly absorb fluids insulted into absorbent composites, and can retain such fluids to prevent leakage and help provide a dry feel even after fluid insult.

A variety of materials have been described for use as absorbent materials in absorbent articles. Included among these materials are natural-based materials such as agar, pectin, gums, carboxyalkyl starch and carboxyalkyl cellulosic, such as carboxymethyl cellulose. Natural-based materials tend to form gels rather than maintaining a solid form and are therefore typically not favored in these products. Synthetic materials such as sodium salts of polyacrylates, polyacrylamides, and hydrolyzed polyacrylonitriles have also been used as absorbent materials in absorbent articles. Although natural-based absorbing materials are well known, these materials have not gained wide usage in absorbent articles because of their relatively inferior absorbent properties compared to synthetic absorbent materials, such as sodium polyacrylates. The relatively high cost of these materials has also precluded their use in consumer absorbent products. Furthermore, many natural-based materials tend to form soft, gelatinous masses when swollen with a liquid. The presence of such gelatinous masses in a product's core tends to limit liquid intake, transport and distribution within the core and prevents subsequent liquid insults from being efficiently and effectively absorbed by the product.

In contrast to the natural-based absorbents, synthetic absorbent materials are generally capable of absorbing large quantities of liquid while maintaining a relatively non-gelatinous form. Synthetic absorbent materials, often referred to as superabsorbent polymers ("SAP"), have been incorporated into absorbent composites to provide higher absorbency under pressure and higher absorbency per gram of absorbent material. Superabsorbent polymers are generally supplied as particles having a diameter in the range from about 20-800 microns. Due to their high absorbent capacity under load, absorbent composites that include superabsorbent polymer particles provide the benefit of skin dryness. Because superabsorbent polymer particles can absorb many times their weight in liquid under load, these particles provide the further significant advantages of thinness and wearer comfort. In addition, superabsorbent polymer particles are about half the cost per gram of liquid absorbed under load compared to fluff pulp fibers. For these reasons it is not surprising that there is a growing trend toward higher superabsorbent particle levels and reduced levels of fluff pulp in consumer absorbent products. In fact, some infant diapers for example include 60 to 70 percent by weight ("wt %") superabsorbent polymer in their liquid storage core. From a cost perspective, an absorbent composite made from 100 wt % superabsorbent particles may be desirable. However, as noted above, such a composite would typically fail to function satisfactorily due to the absence of any significant liquid wicking and distribution of acquired liquid throughout the absorbent composite.

Furthermore, such a composite would tend to lack strength to retain its wet and/or dry structure, shape, and integrity. For example, as superabsorbent content in these products is increased, the absorbent composite suffers in terms of fluid wicking capability as well as wet integrity. When superabsorbent particle content in an absorbent composite is higher than 50 wt %, and particularly as the superabsorbent particle content draws closer to 100 wt %, the absorbent composite exhibits a limited capability of wicking fluid (a function typically performed by fluff) which reduces significantly its utilization efficiency. At the same time, such absorbent composites tend to have almost no wet integrity, particularly after the product is fully loaded with fluid. In order to improve wet integrity of the absorbent composite having high content of superabsorbent particles, binder fiber or adhesive material is often used which can help improve integrity, but at the cost of further reducing fluid wicking capability since the binder fiber and adhesive material are generally hydrophobic in nature. In addition, such materials could add cost to the product.

Another drawback concerning synthetic superabsorbent polymers is their lack of ability to biodegrade. The synthetic polymers' non-biodegradability is disadvantageous with regard to the disposal of used absorbent products containing these polymers.

Cellulosic fibers provide absorbent products with critical functionality that has, to date, not been duplicated by particulate superabsorbent polymers. For absorbent articles comprising absorbent composites, U.S. southern pine fluff pulp is used most often and is often the preferred fiber for such composites. The preference is based on the fluff pulp's advantageous high fiber length (about 2.8 mm) and its relative ease of processing from a wetlaid pulp sheet to an airlaid web. However, these fluff pulp fibers typically only absorb about 2-3 g/g of liquid (e.g., water, saline or bodily fluids) within the fibers' cell walls. Most of the fibers' liquid holding capacity resides in the interstices between fibers. For this reason, a fibrous matrix readily releases acquired liquid on application of pressure. The tendency to release acquired liquid can result in significant skin wetness during use of an absorbent article that includes an absorbent composite formed exclusively from cellulosic fibers. Such articles also tend to leak acquired liquid because liquid is not effectively retained in such a fibrous absorbent composite. This, in turn, reduces product performance as well as confidence by the user.

In some instances, superabsorbent materials have been introduced in synthetic fiber form seeking to provide a material having the functionality of both fiber and superabsorbent polymer particles. However, these superabsorbent fibers are not biodegradable and are difficult to process compared to fluff pulp fibers. In addition, they tend not to blend well with fluff pulp fibers. Furthermore, synthetic superabsorbent fibers are significantly more expensive than superabsorbent polymer particles and, as a result, have not competed effectively for high volume use in absorbent articles.

Attempts have been made to render cellulosic fibers highly absorptive regeneration and by chemical modification to include ionic groups such as carboxylic acid, sulfonic acid, and quaternary ammonium groups that impart water swellability to the fiber. Although some of these modified cellulosic materials are soluble in water, some are water-insoluble. Regardless, none of these highly absorptive modified cellulosic materials possess the structure of a pulp fiber. Rather, these modified cellulosic materials are typically granular or have a regenerated fibril form.

Accordingly, a need exists for a highly absorbent material suitable for use in absorbent articles, where the absorbent material has absorptive properties similar to synthetic, highly absorptive materials and at the same time offers the advantages of liquid wicking and distribution associated with fluff pulp fibers. There is also a need to have an absorbent composite having a superabsorbent content greater than 50 wt %, such as greater than 60 wt %, or greater than 80 wt %, or greater than 90 wt %, or even up to 100 wt %. An absorbent composite having a high superabsorbent content can mean a thinner, lower mass and low cost product. Therefore, there is a further need to develop an absorbent composite which has improved fluid wicking capability while achieving an improved wet integrity for an absorbent composite comprising as much as 100% superabsorbent material.

In addition, there is a need for an absorbent composite comprising a fibrous superabsorbent that combines the advantageous liquid storage capacity provided by superabsorbent polymers and the advantageous liquid wicking and wet integrity provided by fluff pulp fibers. Ideally, the fibrous superabsorbent would be economically viable for use in absorbent articles and would be biodegradable thereby making the disposal of used absorbent products environmentally friendly.

SUMMARY

In response to the needs discussed above, an absorbent absorbent article comprises an absorbent composite. In some aspects, the absorbent composite comprises substantially water-insoluble, water-swellable, non-regenerated, carboxyalkyl cellulose fibers; where the substantially water-insoluble, water-swellable, non-regenerated, carboxyalkyl cellulose fibers have a surface having the appearance of the surface of a cellulose fiber; where the substantially water-insoluble, water-swellable, non-regenerated, carboxyalkyl cellulose fibers comprise a plurality of first intra-fiber multi-valent metal ion crosslinks and a plurality of second intra-fiber crosslinks selected from ether crosslinks or ester crosslinks; and where the absorbent composite has been subjected to a treatment to create interfiber bonding.

In some aspects, the absorbent composite comprises from 90 wt % to 100 wt % of the substantially water-insoluble, water-swellable, non-regenerated, carboxyalkyl cellulose fibers. In some aspects, the multi-valent metal ion crosslinks of the fibers comprise one or more metal ions selected from the group consisting of aluminum, boron, bismuth, titanium, zirconium, cerium, and chromium ions, and mixtures thereof. In some aspects, the second crosslinks of the fibers are from 1,3-dichloro-2-propanol.

In some aspects, the interfiber bonding of the absorbent composite is present throughout the absorbent composite. In other aspects, the interfiber bonding is present only on the surface of the absorbent composite. In some aspects, the interfiber bonding of the absorbent composite will be formed prior to incorporation into an absorbent article. In other aspects, the interfiber bonding of the absorbent composite will be formed in-situ upon wetting due to the treatment.

In some aspects, the treatment for the absorbent composite is in the form of an alcohol/water solution. In other aspects, the treatment for the absorbent composite is in the form of a cationic polymer/alcohol/water solution. In some aspects, the alcohol is selected from ethanol or isopropanol. In some aspects, the alcohol is present in the solution in an amount between about 50 wt % and 70 wt %. In some aspects, the absorbent composite has been dried to about 88-92 wt % solids prior to the treatment.

In some aspects, the absorbent composite exhibits a vertical fluid wicking distance at least about 5 inches a 0.9 wt % sodium chloride aqueous solution as measured by the Vertical Wicking Test.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

Figure 1:
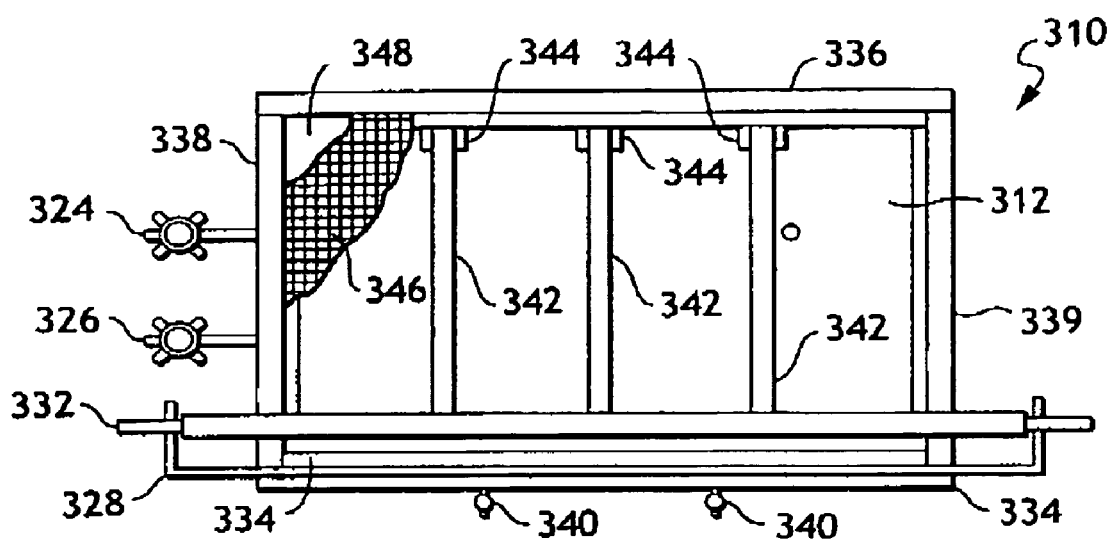
FIG. 1 is a partially cut away top view of a Saturated Capacity tester.

Repeated use of reference characters in the present specification and drawings is intended to represent the same or analogous features or elements of the present invention.

TEST METHODS

Centrifuge Retention Capacity (CRC) Test

The Centrifuge Retention Capacity (CRC) Test measures the ability of the absorbent sample to retain liquid therein after being saturated and subjected to centrifugation under controlled conditions. The resultant retention capacity is stated as grams of liquid retained per gram weight of the sample (g/g). For the fiber samples, the sample to be tested is used as is.

The retention capacity is measured by placing 0.2±0.005 grams of the sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch (12.7 cm×7.6 cm) sample of the bag material in half and heat-sealing two of the open edges to form a 2.5-inch by 3-inch (6.4 cm×7.6 cm) rectangular pouch. The heat seals should be about 0.25 inches (0.6 cm) inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three (3) minutes of preparation unless immediately placed in a sealed container, in which case the filled bags must be tested within thirty (30) minutes of preparation.

The bags are placed between two TEFLON coated fiberglass screens having 3 inch (7.6 cm) openings (available from Taconic Plastics, Inc., having a place of business in Petersburg, N.Y., U.S.A.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LABOFUGE 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$CRC = \frac{\text{sample/bag wt. after centrifuge} - \text{empty bag wt. after centrifuge} - \text{dry sample wt.}}{\text{dry sample wt.}}$$

The three samples are tested and the results are averaged to determine the centrifuge retention capacity (CRC). The samples are tested at 23±1° C. at 50±9% relative humidity.

Free Swell Capacity Test

The materials, procedure, and calculations to determine free swell capacity (g/g) and centrifuge retention capacity (CRC) (g/g) were as follows.

Test Materials:

Pre-made empty tea bags (available from Drugstore.com, IN PURSUIT OF TEA polyester tea bags 93 mm×70 mm with fold-over flap, found at http:www.mesh.nejp/tokiwa/). Balance (4 decimal place accuracy, 0.0001 g for air-dried superabsorbent (ADS) and tea bag weights); timer; 1% saline; drip rack with clips (NLM 211).

Test Procedure:

1. Determine solids content of ADS.
2. Pre-weigh tea bags to nearest 0.0001 g and record.

3. Accurately weigh 0.2025 g+/−0.0025 g of test material (superabsorbent), record and place into pre-weighed tea bag (air-dried (AD) bag weight). (ADS weight+AD bag weight=total dry weight).
4. Fold tea bag edge over closing bag.
5. Fill a container (at least 3 inches (7.6 cm) deep) with at least 2 inches (5.1 cm) with 1% saline.
6. Hold tea bag (with test sample) flat and shake to distribute test material evenly through bag.
7. Lay tea bag onto surface of saline and start timer.
8. Soak bags for specified time (e.g., 30 minutes).
9. Remove tea bags carefully, being careful not to spill any contents from bags, hang from a clip on drip rack for 3 minutes.
10. Carefully remove each bag, weigh, and record (drip weight).

Calculations:

The tea bag material has an absorbency determined as follows:

Free Swell Capacity, factor=5.78

$Z$=Oven dry superabsorbent wt($g$)/Air dry superabsorbent wt($g$)

Free Capacity (g/g):

$$\frac{[(\text{drip wt (g)} - \text{dry bag wt (g)}) - (AD\ SAP\ \text{wt (g)})] - (\text{dry bag wt (g)} * 5.78)}{(AD\ SAP\ \text{wt (g)} * Z)}$$

Saturated Capacity (SAT CAP) Test

Figure 2:
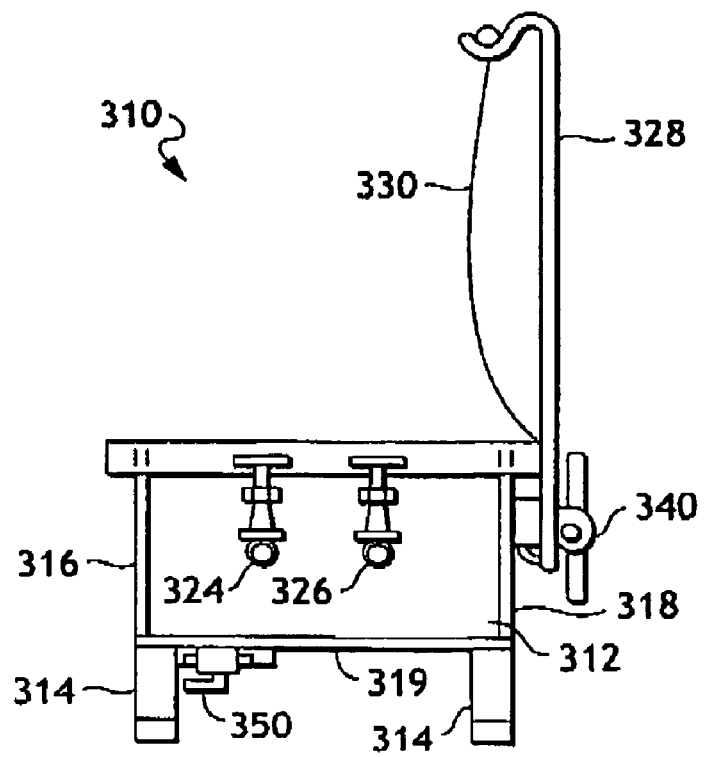
FIG. 2 is a side view of a Saturated Capacity tester.
Figure 3:
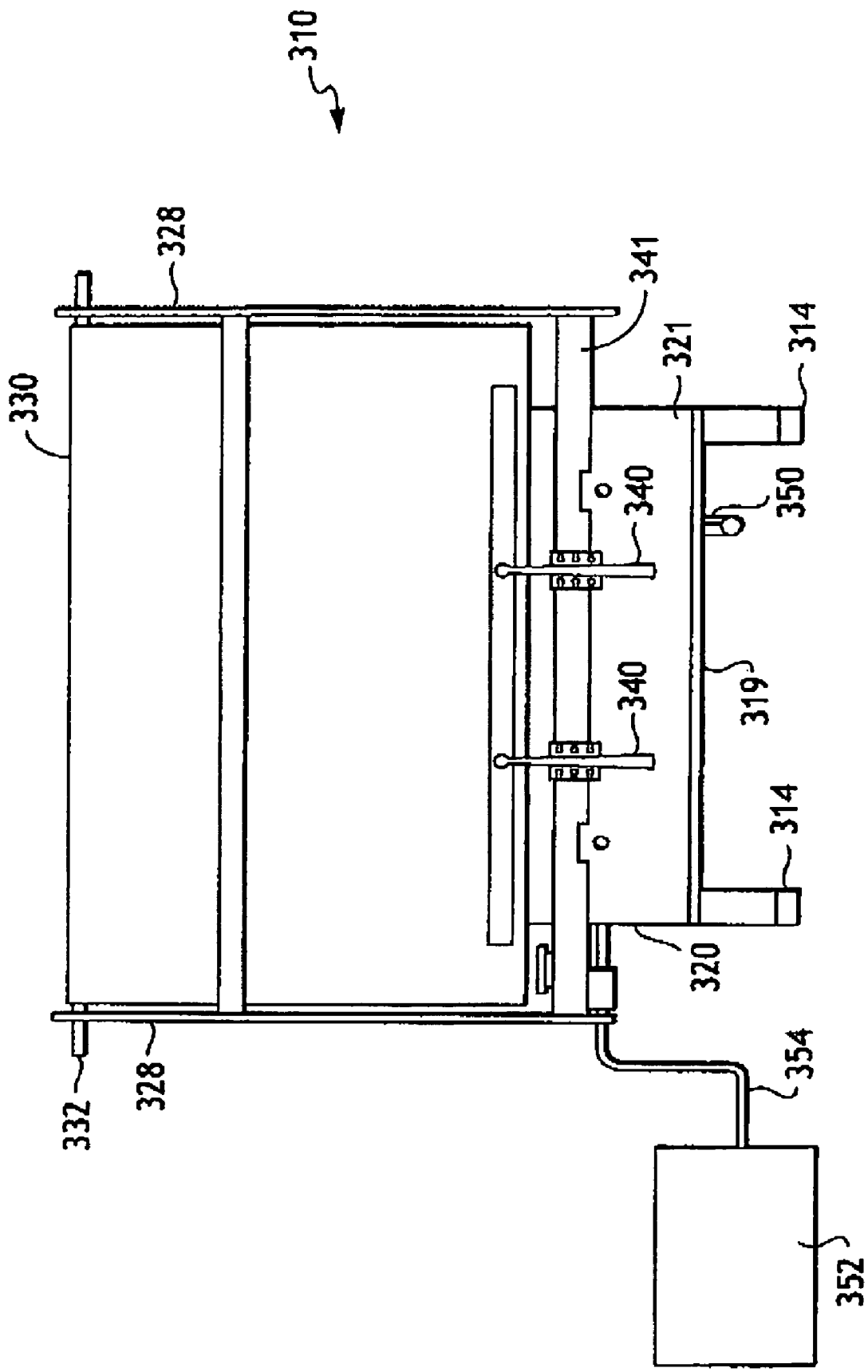
FIG. 3 is a rear view of a Saturated Capacity tester.

Saturated Capacity is determined using a Saturated Capacity (SAT CAP) tester with a Magnahelic vacuum gage and a latex dam, comparable to the following description. Referring to FIGS. 1-3, a Saturated Capacity tester vacuum apparatus 310 comprises a vacuum chamber 312 supported on four leg members 314. The vacuum chamber 312 includes a front wall member 316, a rear wall member 318, and two side walls 320 and 321. The wall members are sufficiently thick to withstand the anticipated vacuum pressures, and are constructed and arranged to provide a chamber having outside dimensions measuring 23.5 inches (59.7 cm) in length, 14 inches (35.6 cm) in width and 8 inches (20.3 cm) in depth.

A vacuum pump (not shown) operably connects with the vacuum chamber 312 through an appropriate vacuum line conduit and a vacuum valve 324. In addition, a suitable air bleed line connects into the vacuum chamber 312 through an air bleed valve 326. A hanger assembly 328 is suitably mounted on the rear wall 318 and is configured with S-curved ends to provide a convenient resting place for supporting a latex dam sheet 330 in a convenient position away from the top of the vacuum apparatus 310. A suitable hanger assembly can be constructed from 0.25 inch (0.64 cm) diameter stainless steel rod. The latex dam sheet 330 is looped around a dowel member 332 to facilitate grasping and to allow a convenient movement and positioning of the latex dam sheet 330. In the illustrated position, the dowel member 332 is shown supported in a hanger assembly 328 to position the latex dam sheet 330 in an open position away from the top of the vacuum chamber 312.

A bottom edge of the latex dam sheet 330 is clamped against a rear edge support member 334 with suitable securing means, such as toggle clamps 340. The toggle clamps 340 are mounted on the rear wall member 318 with suitable spacers 341 which provide an appropriate orientation and alignment of the toggle clamps 340 for the desired operation. Three support shafts 342 are 0.75 inches in diameter and are removably mounted within the vacuum chamber 312 by means of support brackets 344. The support brackets 344 are generally equally spaced along the front wall member 316 and the rear wall member 318 and arranged in cooperating pairs. In addition, the support brackets 344 are constructed and arranged to suitably position the uppermost portions of the support shafts 342 flush with the top of the front, rear and side wall members of the vacuum chamber 312. Thus, the support shafts 342 are positioned substantially parallel with one another and are generally aligned with the side wall members 320 and 321. In addition to the rear edge support member 334, the vacuum apparatus 310 includes a front support member 336 and two side support members 338 and 339. Each side support member measures about 1 inch (2.5 cm) in width and about 1.25 inches (3.2 cm) in height. The lengths of the support members are constructed to suitably surround the periphery of the open top edges of the vacuum chamber 312, and are positioned to protrude above the top edges of the chamber wall members by a distance of about 0.5 inches.

A layer of egg crating type material 346 is positioned on top of the support shafts 342 and the top edges of the wall members of the vacuum chamber 312. The egg crate material extends over a generally rectangular area measuring 23.5 inches (59.7 cm) by 14 inches (35.6 cm), and has a depth measurement of about 0.38 inches (1.0 cm). The individual cells of the egg crating structure measure about 0.5 inch square, and the thin sheet material comprising the egg crating is composed of a suitable material, such as polystyrene. For example, the egg crating material can be McMaster-Carr Supply Catalog No. 162 4K 14 (available from McMaster-Carr Supply Company, having a place of business in Atlanta, Ga. U.S.A.) translucent diffuser panel material. A layer of 6 mm (0.24 inch) mesh TEFLON-coated screening 348 (available from Eagle Supply and Plastics, Inc., having a place of business in Appleton, Wis., U.S.A.) which measures 23.5 inches (59.7 cm) by 14 inches (35.6 cm), is placed on top of the egg crating material 346.

A suitable drain line and a drain valve 350 connect to the bottom plate member 319 of the vacuum chamber 312 to provide a convenient mechanism for draining liquids from the vacuum chamber 312. The various wall members and support members of the vacuum apparatus 310 may be composed of a suitable non-corroding, moisture-resistant material, such as polycarbonate plastic. The various assembly joints may be affixed by solvent welding and/or fasteners, and the finished assembly of the tester is constructed to be water-tight. A vacuum gauge 352 operably connects through a conduit into the vacuum chamber 312. A suitable pressure gauge is a Magnahelic differential gauge capable of measuring a vacuum of 0-100 inches of water, such as a No. 2100 gauge available from Dwyer Instrument Incorporated (having a place of business in Michigan City, Ind., U.S.A.)

The dry product or other absorbent structure is weighed and then placed in excess 0.9% NaCl saline solution, submerged and allowed to soak for twenty (20) minutes. After the twenty (20) minute soak time, the absorbent structure is placed on the egg crate material and mesh TEFLON-coated screening of the Saturated Capacity tester vacuum apparatus 310. The latex dam sheet 330 is placed over the absorbent structure(s) and the entire egg crate grid so that the latex dam sheet 330 creates a seal when a vacuum is drawn on the vacuum apparatus 310. A vacuum of 0.5 pounds per square inch (psi) is held in the Saturated Capacity tester vacuum apparatus 310 for five minutes. The vacuum creates a pressure on the absorbent structure(s), causing drainage of some liquid. After five minutes at 0.5 psi vacuum, the latex dam sheet 330 is rolled back and the absorbent structure(s) are weighed to generate a wet weight.

The overall capacity of each absorbent structure is determined by subtracting the dry weight of each absorbent from the wet weight of that absorbent, determined at this point in the procedure. The 0.5 psi Saturated Capacity or Saturated Capacity of the absorbent structure is determined by the following formula:

$$\text{Saturated Capacity} = (\text{wet weight} - \text{dry weight})/\text{dry weight};$$

wherein the Saturated Capacity value has units of grams of fluid/gram of absorbent. For Saturated Capacity, a minimum of three specimens of each sample should be tested and the results averaged. If the absorbent structure has low integrity or disintegrates during the soak or transfer procedures, the absorbent structure can be wrapped in a containment material such as paper toweling, for example SCOTT paper towels manufactured by Kimberly-Clark Corporation, having a place of business in Neenah, Wis., U.S.A. The absorbent structure can be tested with the overwrap in place and the capacity of the overwrap can be independently determined and subtracted from the wet weight of the total wrapped absorbent structure to obtain the wet absorbent weight.

When the material to be tested is superabsorbent material, the test is run as set forth above with the following exceptions. A bag is prepared from heat sealable tea bag material (grade 542, commercially available from the Kimberly-Clark Corporation). A six inch by three inch sample of the material is folded in half and heat sealed along two edges to form a generally square pouch. 0.2 grams of the superabsorbent material to be tested (having a moisture content of less than about 5 weight percent) (and if in the form of particles, then having a size within the range of from about 300 to about 600 μm,) is placed in the pouch and the third side is heat sealed. The test is performed as described with the amount of the fluid absorbed by the bag material being subtracted from the amount of fluid retained by the bag and superabsorbent material. The amount of fluid absorbed by the bag material is determined by performing the saturated retention capacity test on an empty bag.

Absorbency Under Load (AUL) Test

The materials, procedure, and calculations to determine AUL were as follows:

Test Materials:

Mettler Toledo PB 3002 balance and BALANCE-LINK software or other compatible balance and software.

Software set-up: record weight from balance every 30 sec (this will be a negative number. Software can place each value into EXCEL spreadsheet.

Kontes 90 mm ULTRA-WARE filter set up with fritted glass (coarse) filter plate, clamped to stand; 2 L glass bottle with outlet tube near bottom of bottle; rubber stopper with glass tube through the stopper that fits the bottle (air inlet); TYGON tubing; stainless steel rod/plexiglass plunger assembly (71 mm diameter); stainless steel weight with hole drill through to place over plunger (plunger and weight=867 g); VWR 9.0 cm filter papers (Qualitative 413 catalog number 28310-048) cut down to 80 mm size; double-stick SCOTCH tape; and 0.9% saline.

Test Procedure:

1. Level filter set-up with small level.
2. Adjust filter height or fluid level in bottle so that flitted glass filter and saline level in bottle are at same height.
3. Make sure that there are no kinks in tubing or air bubbles in tubing or under flitted glass filter plate.
4. Place filter paper into filter and place stainless steel weight onto filter paper.
5. Wait for 5-10 min while filter paper becomes fully wetted and reaches equilibrium with applied weight.
6. Zero balance.
7. While waiting for filter paper to reach equilibrium prepare plunger with double stick tape on bottom.
8. Place plunger (with tape) onto separate scale and zero scale.
9. Place plunger into dry test material so that a monolayer of material is stuck to the bottom by the double stick tape.
10. Weigh the plunger and test material on zeroed scale and record weight of dry test material (dry material weight 0.15 g +/−0.05 g).
11. Filter paper should be at equilibrium by now, zero scale.
12. Start balance recording software.
13. Remove weight and place plunger and test material into filter assembly.
14. Place weight onto plunger assembly.
15. Wait for test to complete (30 or 60 min)
16. Stop balance recording software.

Calculations:

$A$ = balance reading $(g)*-1$ (weight of saline absorbed by test material)

$B$ = dry weight of test material (this can be corrected for moisture by multiplying the AD weight by solids %).

$\text{AUL}(g/g) = A/B$ ($g$ 1% saline/1 $g$ test material)

Fluid Intake Flowback Evaluation (FIFE) Test

Figure 4:
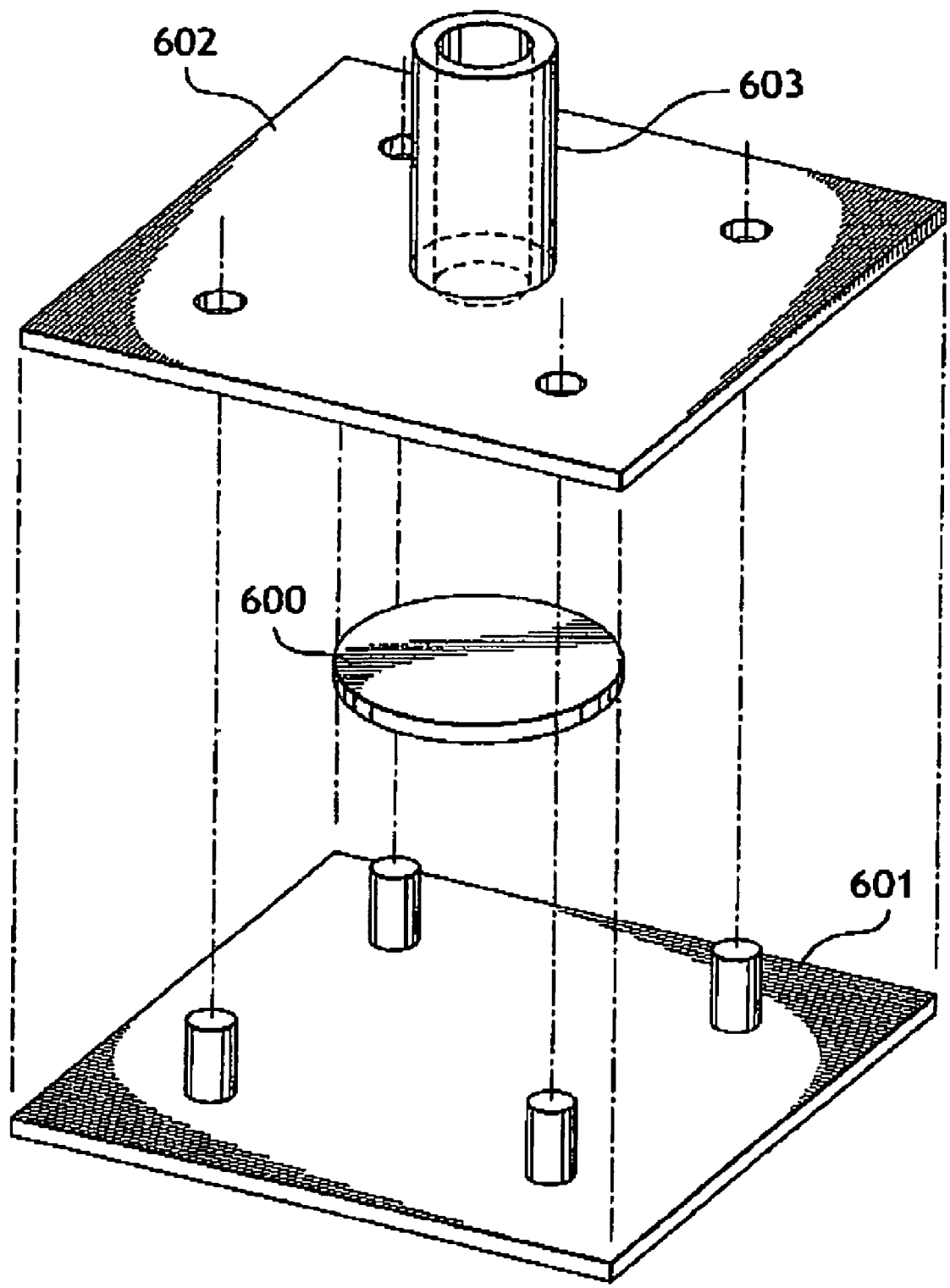
FIG. 4 is a perspective view of the test apparatus employed for the Fluid Intake Flowback Evaluation Test.

The fluid intake flowback evaluation (FIFE) test determines the amount of time required for an absorbent composite to intake a predetermined amount of liquid. A suitable apparatus for performing the FIFE test is shown in FIG. 4.

The samples for testing are prepared from fibers to be tested by distributing by hand approximately 2.5 g fiber into a 3 inch (7.6 cm) circular mold to form a uniform pad. A plunger is placed on top of the pad and the pad pressed to a final caliper of approximately 2.5 mm. The 3 inch (7.6 cm) circular pads including forming tissue on the top and bottom of the pad sample (composite 600).

Composite 600 is centered on FIFE test plate 601. Top 602 is then placed onto plate 601 with composite 600 centered under insult cylinder 603. Top 602 weighs 360 g providing a testing load of 0.11 psi on the sample when top 602 is in place for the test. Plate 601 and top 602 with cylinder 603 are made from PLEXIGLAS (approximate dimensions of 17.8 cm×17.8 cm). Insult cylinder 603 has an inner diameter of one inch, a length sufficient to receive at least 15 g liquid, and provides for communication of liquid to composite 600.

Prior to testing, the sample (composite 600) is weighed and its weight recorded, and the sample's bulk is measured at 0.05 psi and recorded.

In the test procedure, the sample (composite 600) is centered on plate 601 and top 602 is applied. Once the sample is in place and the apparatus assembled, the sample is ready for FIFE testing. Prior to running the FIFE test, the aforementioned Saturated Capacity Test is measured on the sample 600. Thirty percent (30%) of the saturation capacity is then calculated by multiplying the mass of the dry sample (grams) times the measured saturated capacity (gram/gram) times 0.3. Time zero is the time that the liquid first contacts the sample. The first insult time is measured as the time required for the first added liquid to be absorbed by the sample (i.e., liquid level drops below upper forming tissue of sample). After 15 minutes, a second insult is delivered by adding 15 g of 0.9% saline (second insult) to the cylinder and the sample. The second insult time is measured as the time required for the second added liquid to be absorbed by the sample. After 30 minutes, the third insult (15 g of 0.9% saline) is delivered and the third insult time measured, and after 45 minutes, the fourth insult (15 g of 0.9% saline) is delivered and the fourth insult time measured.

Vertical Wicking Test

Each sample is cut into a 1.5 inch by 7 inch (3.8 cm×17.8 cm) strip. Each strip is weighed and the sample dry weight is recorded by weighing the sample on a scale. Each strip is then hung (by a suitable hanger device) vertically by its top end with its lower end just barely contacting the surface of at least 500 ml of 0.9% NaCl saline contained in a liquid reservoir. Each strip is allowed to remain in contact with the saline in the vertical position for 30 minutes. After the 30 minutes has been completed, the wicking distance is noted by measuring the distance that liquid has risen in the vertical sample by utilizing a ruler, and the sample wet weight of each sample is then recorded by weighing the wet sample on a scale. The wicking capacity is then calculated by subtracting the dry sample weight from the wet sample weight.

Wet Integrity

The wet integrity of each sample is assessed during the Vertical Wicking Test described above. In particular, after each strip has been in contact with the saline for 30 minutes, the sample is removed from the hanger and grasped between a person's thumb and forefinger and then gently shaken several times. If the sample breaks or falls apart, its wet integrity is recorded as zero. If the sample holds together without changing shape after being gently shaken several times, its wet integrity is recorded as a five.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "bulk crosslinked" refers to a fiber of the present invention having its molecular chains present throughout the fiber formed by a compound applied thereto, often during formation of the fiber. The term "bulk crosslinking" means that the functional crosslinks can be substantially throughout the interior of the fiber, as well as the exterior of the fiber.

The term "coform" is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent materials. The meltblown fibers containing wood fibers and/or other materials are collected on a forming surface, such as provided by a foraminous belt. The forming surface may include a gas-pervious material, such as spunbonded fabric material, that has been placed onto the forming surface.

The terms "elastic," "elastomeric," "elastically" and "elastically extensible" are used interchangeably to refer to a material or composite that generally exhibits properties which approximate the properties of natural rubber. The elastomeric material is generally capable of being extended or otherwise deformed, and then recovering a significant portion of its shape after the extension or deforming force is removed.

The term "extensible" refers to a material that is generally capable of being extended or otherwise deformed, but which does not recover a significant portion of its shape after the extension or deforming force is removed.

The terms "fluid impermeable," "liquid impermeable," "fluid impervious" and "liquid impervious" mean that fluid such as water or bodily fluids will not pass substantially through the layer or laminate under ordinary use conditions in a direction generally perpendicular to the plane of the layer or laminate at the point of fluid contact.

The terms "hydrophilic" and "wettable" are used interchangeably to refer to a material having a contact angle of water in air of less than 90 degrees. The term "hydrophobic" refers to a material having a contact angle of water in air of at least 90 degrees. For the purposes of this application, contact angle measurements are determined as set forth in Robert J. Good and Robert J. Stromberg, Ed., in "Surface and Colloid Science—Experimental Methods," Vol. 11, (Plenum Press, 1979), which is hereby incorporated by reference in a manner that is consistent herewith.

The term "layer" when used in the singular can have the dual meaning of a single element or a plurality of elements.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other materials are carried by the high velocity gas stream and are deposited on a collecting surface. The distribution and orientation of the meltblown fibers within the formed web is dependent on the geometry and process conditions. Under certain process and equipment conditions, the resulting fibers can be substantially "continuous," defined as having few separations, broken fibers or tapered ends when multiple fields of view are examined through a microscope at 10× or 20× magnification. When "continuous" melt blown fibers are produced, the sides of individual fibers will generally be parallel with minimal variation in fiber diameter within an individual fiber length. In contrast, under other conditions, the fibers can be overdrawn and strands can be broken and form a series of irregular, discrete fiber lengths and numerous broken ends. Retraction of the once attenuated broken fiber will often result in large clumps of polymer.

The term "polyolefin" as used herein generally includes, but is not limited to, materials such as polyethylene, polypropylene, polyisobutylene, polystyrene, ethylene vinyl acetate copolymer and the like, the homopolymers, copolymers, terpolymers, etc., thereof, and blends and modifications thereof. The term "polyolefin" shall include all possible structures thereof, which includes, but is not limited to, isotatic, synodiotactic and random symmetries. Copolymers include random and block copolymers.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "stretchable" refers to materials which may be extensible or which may be elastically extensible.

The terms "superabsorbent" refers to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride.

The terms "surface treated" and "surface crosslinked" refer to a fiber of the present invention having its molecular chains present in the vicinity of the fiber surface crosslinked by a compound applied to the surface of the fiber. The term "surface crosslinking" means that the functional crosslinks are in the vicinity of the surface of the fiber. As used herein, "surface" describes the outer-facing boundaries of the fiber.

The term "target zone" refers to an area of an absorbent core where it is particularly desirable for the majority of a fluid insult, such as urine, menses, or bowel movement, to initially contact. In particular, for an absorbent core with one or more fluid insult points in use, the insult target zone refers to the area of the absorbent core extending a distance equal to 15% of the total length of the composite from each insult point in both directions.

The term "thermoplastic" describes a material that softens when exposed to heat and which substantially returns to a non-softened condition when cooled to room temperature.

The term "% by weight" or "wt %" when used herein and referring to components of the superabsorbent polymer composition, is to be interpreted as based on the dry weight of the superabsorbent polymer composition, unless otherwise specified herein.

These terms may be defined with additional language in the remaining portions of the specification.

DETAILED DESCRIPTION

An absorbent article of the present invention can comprise an absorbent composite. In some aspects, the absorbent composite can function as an absorbent core component of an absorbent article. In other aspects, the absorbent composite by itself can function as the absorbent article. In some aspects, the absorbent article can comprise additional components. For example, absorbent articles can have a topsheet and/or a backsheet. In some aspects, the absorbent article can comprise an absorbent composite disposed between a topsheet and a backsheet. In some aspects, at least one component of the article, such as the absorbent composite, includes substantially water-insoluble, water-swellable, non-regenerated, carboxyalkyl cellulose fibers, where the fibers have a surface having the appearance of the surface of a cellulose fiber, and where the fibers comprise a plurality of non-permanent intra-fiber metal crosslinks and a plurality of permanent intra-fiber crosslinks. In some aspects, the fiber has a plurality of non-permanent intra-fiber metal crosslinks formed on the surface of the fiber and a plurality of permanent intra-fiber crosslinks formed throughout the fiber. In other aspects, the fiber has a plurality of permanent intra-fiber crosslinks formed on the surface of the fiber and a plurality of permanent intra-fiber crosslinks formed throughout the fiber.

In some aspects, at least one component of the article, such as the absorbent composite, includes substantially water-insoluble, water-swellable, non-regenerated, carboxyalkyl cellulose fibers, where the fibers have a surface having the appearance of the surface of a cellulose fiber, and where the fibers comprise a plurality of non-permanent intra-fiber metal crosslinks and a plurality of permanent intra-fiber crosslinks, where the permanent intra-fiber crosslinks comprise covalent crosslinks formed from 1,3-dichloro-2-propanol. In still other aspects, at least one component of the article, such as the absorbent composite, includes a fiber bundle comprising a plurality of substantially water-insoluble, water-swellable, non-regenerated, carboxyalkyl cellulose fibers, where the fibers have a surface having the appearance of the surface of a cellulose fiber, and where the fibers comprise a plurality of non-permanent intra-fiber metal crosslinks and a plurality of permanent intra-fiber crosslinks.

In desirable aspects, the composite of the present invention has been subjected to a treatment to create interfiber bonding within the composite. In other aspects, the interfiber bonding is only present on a surface of the absorbent composite. In some aspects, the treatment is an alcohol/water solution. In other aspects, the treatment is a cationic polymer/alcohol/water solution. In some aspects, the alcohol is selected from ethanol or isopropanol. In some particular aspects, the alcohol is present in the solution in an amount between about 50 wt % and 70 wt %. In some aspects, the treatment occurs once the composite has been dried to at least 80 wt % solids. In particular aspects, the treatment occurs once the composite has been dried to between 88 and 92 wt % solids. In some aspects, the absorbent composite comprises from 90 wt % to 100 wt % of the substantially water-insoluble, water-swellable, non-regenerated, carboxyalkyl cellulose fibers.

In some aspects, at least one of the topsheet, backsheet, and absorbent composite is stretchable. In other aspects, the absorbent composite can comprise layers, at least one of which includes substantially the superabsorbent polymer fibers of the present invention and at least one of which includes substantially fluff and/or superabsorbent polymer particles.

Figure 5:
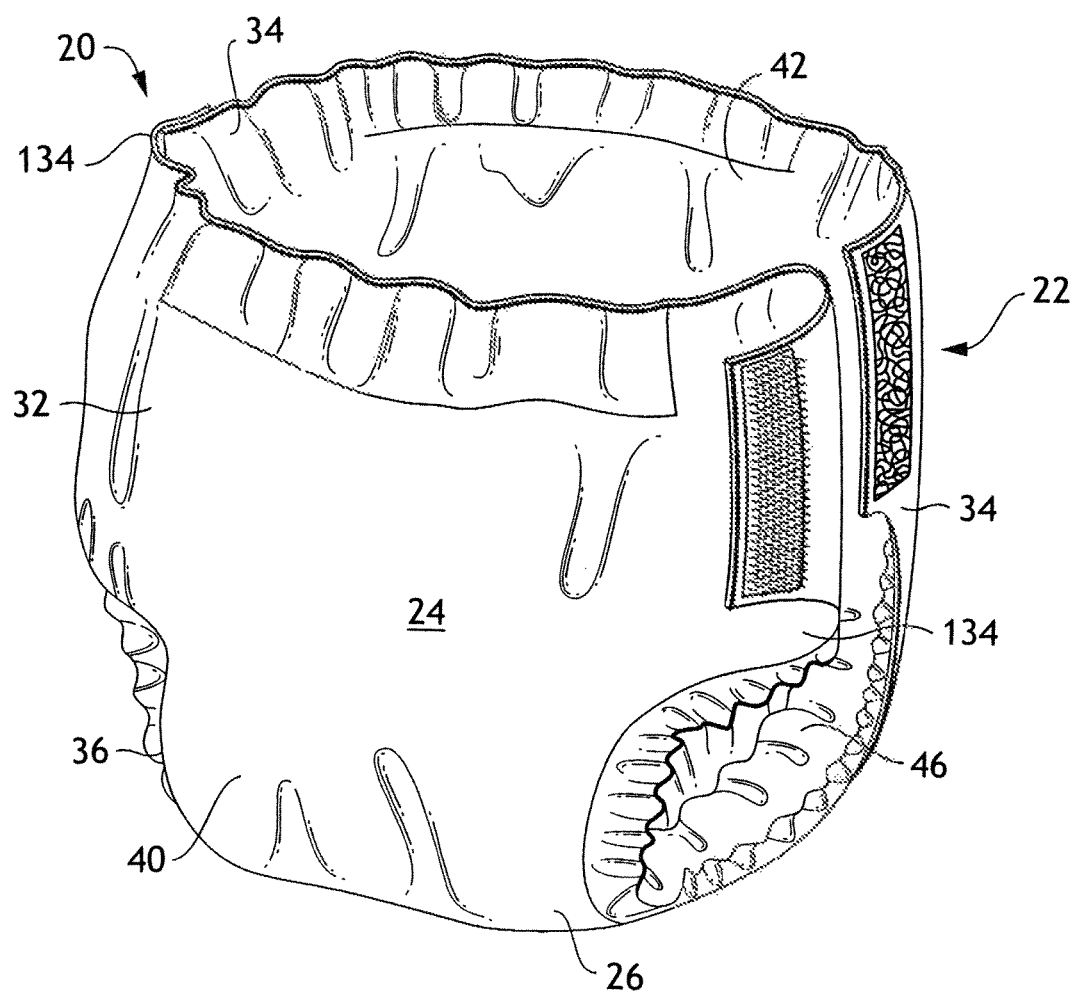
FIG. 5 is a perspective view of one embodiment of an absorbent article that may be made in accordance with the present invention.
Figure 6:
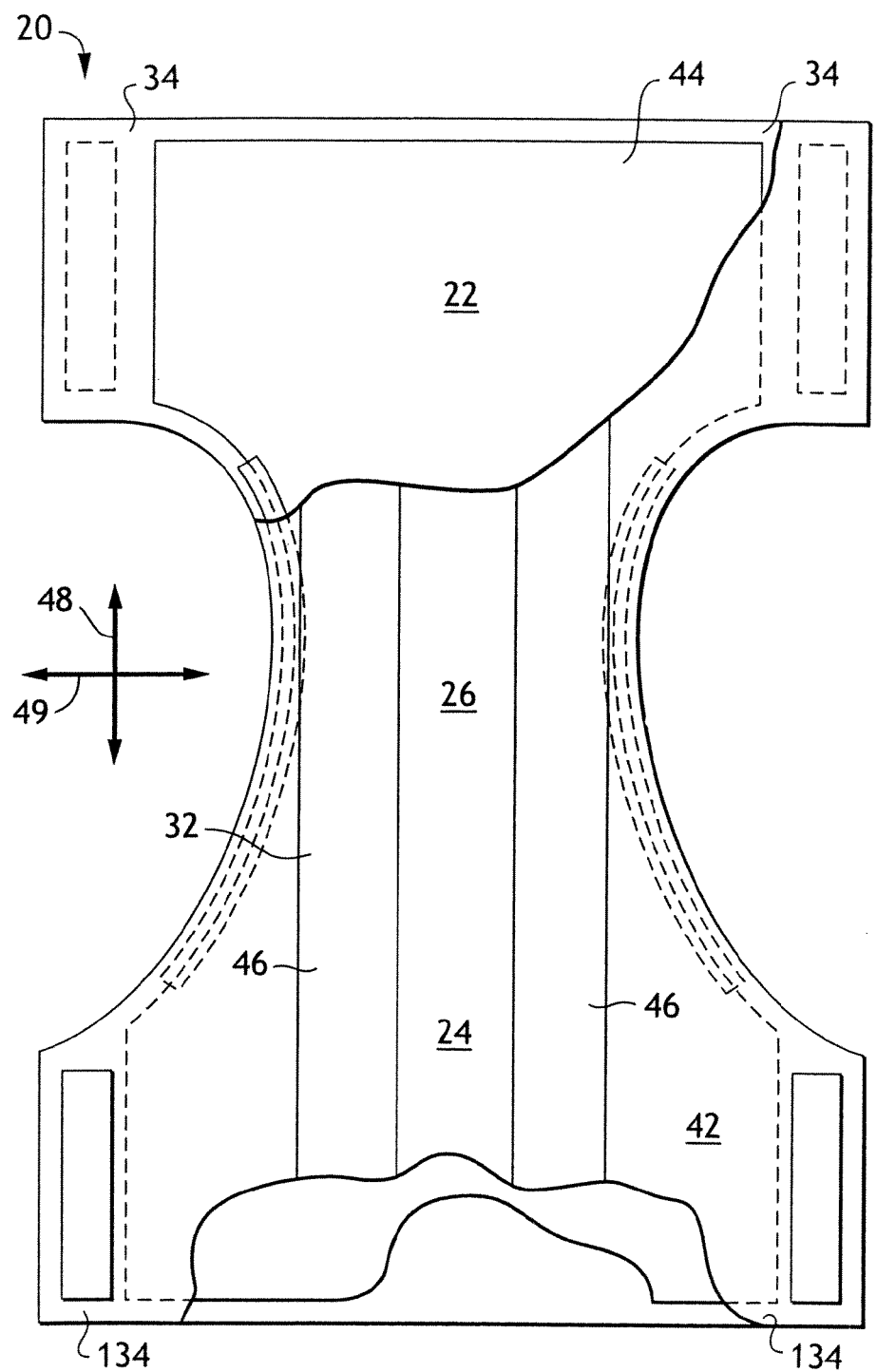
FIG. 6 is a plan view of the absorbent article shown in FIG. 6 with the article in an unfastened, unfolded and laid flat condition showing the surface of the article that faces the wearer when worn and with portions cut away to show underlying features.

To gain a better understanding of the present invention, attention is directed to FIG. 5 and FIG. 6 for exemplary purposes showing a training pant of the present invention. It is understood that the present invention is suitable for use with various other absorbent articles, without departing from the scope of the present invention.

Various materials and methods for constructing training pants are disclosed in PCT Patent Application No. WO 00/37009 published Jun. 29, 2000 by A. Fletcher et al.; U.S. Pat. No. 4,940,464 to Van Gompel et al.; U.S. Pat. No. 5,766,389 to Brandon et al., and U.S. Pat. No. 6,645,190 to Olson et al., all of which are incorporated herein by reference in a manner that is consistent herewith.

FIG. 5 illustrates a training pant in a partially fastened condition, and FIG. 6 illustrates a training pant in an opened and unfolded state. The training pant defines a longitudinal direction 48 that extends from the front of the training pant when worn to the back of the training pant. Perpendicular to the longitudinal direction 48 is a lateral direction 49.

The pair of training pants defines a front region 22, a back region 24, and a crotch region 26 extending longitudinally between and interconnecting the front and back regions. The pant also defines an inner surface adapted in use (e.g., positioned relative to the other components of the pant) to be disposed toward the wearer, and an outer surface opposite the inner surface. The training pant has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 134 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent composite 44 such as shown in FIG. 6 disposed between the backsheet 40 and the topsheet 42 for absorbing fluid body exudates exuded by the wearer, and may further include a pair of containment flaps 46 secured to the topsheet 42 or the absorbent composite 44 for inhibiting the lateral flow of body exudates.

The backsheet 40, the topsheet 42 and the absorbent composite 44 may be made from many different materials known to those skilled in the art. All three layers, for instance, may be extensible and/or elastically extensible. Further, the stretch properties of each layer may vary in order to control the overall stretch properties of the product.

The backsheet 40, for instance, may be breathable and/or may be fluid impermeable. The backsheet 40 may be constructed of a single layer, multiple layers, laminates, spunbond fabrics, films, meltblown fabrics, elastic netting, microporous webs or bonded-carded-webs. The backsheet 40, for instance, can be a single layer of a fluid impermeable material, or alternatively can be a multi-layered laminate structure in which at least one of the layers is fluid impermeable.

The backsheet 40 can be biaxially extensible and optionally biaxially elastic. Elastic non-woven laminate webs that can be used as the backsheet 40 include a non-woven material joined to one or more gatherable non-woven webs or films. Stretch Bonded Laminates (SBL) and Neck Bonded Laminates (NBL) are examples of elastomeric composites.

Examples of suitable nonwoven materials are spunbond-meltblown fabrics, spunbond-meltblown-spunbond fabrics, spunbond fabrics, or laminates of such fabrics with films, or other nonwoven webs. Elastomeric materials may include cast or blown films, meltblown fabrics or spunbond fabrics composed of polyethylene, polypropylene, or polyolefin elastomers, as well as combinations thereof. The elastomeric materials may include PEBAX elastomer (available from AtoFina Chemicals, Inc., a business having offices located in Philadelphia, Pa. U.S.A.), HYTREL elastomeric polyester (available from Invista, a business having offices located in Wichita, Kan. U.S.A.), KRATON elastomer (available from Kraton Polymers, a business having offices located in Houston, Tex., U.S.A.), or strands of LYCRA elastomer (available from Invista), or the like, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The topsheet 42 is suitably compliant, soft-feeling and non-irritating to the wearer's skin. The topsheet 42 is also sufficiently liquid permeable to permit liquid body exudates to readily penetrate through its thickness to the absorbent composite 44. A suitable topsheet 42 may be manufactured from a wide selection of web materials, such as porous foams, reticulated foams, apertured plastic films, woven and nonwoven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,641,134 filed to Vukos et al. which is incorporated herein by reference in a manner that is consistent herewith.

The article 20 can optionally further include a surge management layer which may be located adjacent the absorbent composite 44 and attached to various components in the article 20 such as the absorbent composite 44 or the topsheet 42 by methods known in the art, such as by using an adhesive. In general, a surge management layer helps to quickly acquire and diffuse surges or gushes of liquid that may be rapidly introduced into the absorbent structure of the article. The surge management layer can temporarily store the liquid prior to releasing it into the storage or retention portions of the absorbent composite 44. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The article 20 can further comprise an absorbent composite 44. The absorbent composite 44 may have any of a number of shapes. For example, it may have a 2-dimensional or 3-dimensional configuration, and may be rectangular shaped, triangular shaped, oval shaped, race-track shaped, I-shaped, generally hourglass shaped, T-shaped and the like. It is often suitable for the absorbent composite 44 to be narrower in the crotch portion 26 than in the rear 24 or front 22 portion(s). The absorbent composite 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

In some aspects, the absorbent composite 44 can have a significant amount of stretchability. For example, the absorbent composite 44 can comprise a matrix of fibers which includes an operative amount of elastomeric polymer fibers. Other methods known in the art can include attaching superabsorbent polymer particles to a stretchable film, utilizing a nonwoven substrate having cuts or slits in its structure, and the like.

The absorbent composite 44 can be formed using methods known in the art. While not being limited to the specific method of manufacture, the absorbent composite can utilize forming drum systems, for example, see U.S. Pat. No. 4,666,647 entitled APPARATUS AND METHOD FOR FORMING A LAID FIBROUS WEB by K. Enloe et al. which issued May 19, 1987, U.S. Pat. No. 4,761,258 entitled CONTROLLED FORMATION OF LIGHT AND HEAVY FLUFF ZONES by K. Enloe which issued Aug. 2, 1988, U.S. Pat. No. 6,630,088 entitled FORMING MEDIA WITH ENHANCED AIR FLOW PROPERTIES by Venturino et al. which issued Oct. 7, 2003, and U.S. Pat. No. 6,330,735 entitled APPARATUS AND PROCESS FOR FORMING A LAID FIBROUS WEB WITH ENHANCED BASIS WEIGHT CAPABILITY by Hahn et al. which issued Dec. 18, 2001; the entire disclosures of which are incorporated herein by reference in a manner that is consistent herewith. Examples of techniques which can introduce a selected quantity of optional superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990 and U.S. Pat. No. 6,416,697 entitled METHOD FOR OBTAINING A DUAL STRATA DISTRIBUTION OF SUPERABSORBENT IN A FIBROUS MATRIX by Venturino et al. which issued Jul. 9, 2002; the entire disclosures of which are incorporated herein by reference in a manner that is consistent herewith.

In some aspects, a meltblown process can be utilized, such as to form the absorbent composite in a coform line. Exemplary meltblown processes are described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. Nos. 3,849,241 and 5,350,624, all of which are incorporated herein by reference in a manner that is consistent herewith.

To form "coform" materials, additional components are mixed with the meltblown fibers as the fibers are deposited onto a forming surface. For example, the superabsorbent fibers of the present invention and fluff, such as wood pulp fibers, may be injected into the meltblown fiber stream so as to be entrapped and/or bonded to the meltblown fibers. Exemplary coform processes are described in U.S. Pat. No. 4,100,324 to Anderson et al.; U.S. Pat. No. 4,587,154 to Hotchkiss et al.; U.S. Pat. No. 4,604,313 to McFarland et al.; U.S. Pat. No. 4,655,757 to McFarland et al.; U.S. Pat. No. 4,724,114 to McFarland et al.; U.S. Pat. No. 4,100,324 to Anderson et al.; and U.K. Patent No. GB 2,151,272 to Minto et al., each of which is incorporated herein by reference in a manner that is consistent herewith. Absorbent, elastomeric meltblown webs containing high amounts of superabsorbent are described in U.S. Pat. No. 6,362,389 to D. J. McDowall, and absorbent, elastomeric meltblown webs containing high amounts of superabsorbent and low superabsorbent shakeout values are described in pending U.S. patent application Ser. No. 10/883174 to X. Zhang et al., each of which is incorporated herein by reference in a manner that is consistent herewith.

Figure 7:
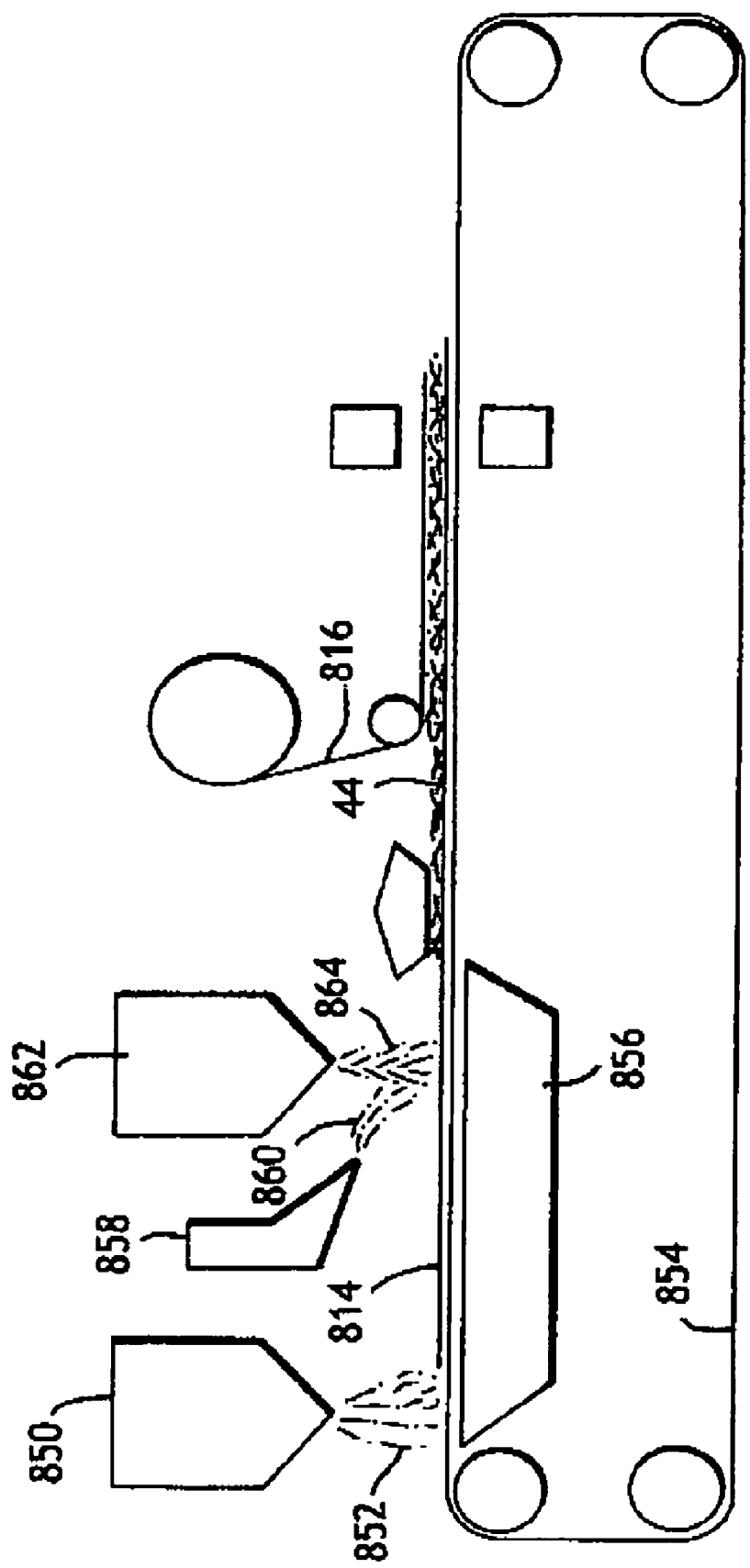
FIG. 7 is a schematic diagram of one version of a method and apparatus for producing an absorbent core.

One example of a method of forming the absorbent composite 44 of the present invention in a single process is illustrated in FIG. 7. First a web is formed using a fiber forming apparatus 850. Superabsorbent fibers 852 of the present invention are deposited onto a forming surface 854 to form a web 814. To further assist in the web formation and to impart better hold-down of the web onto the forming surface 854, a vacuum 856 may be used underneath the foraminous forming surface 854. Optionally, a source 858 of superabsorbent particles or other type particles 860 and optionally a source 862 of fluff fibers 864 may also be deposited onto the forming surface 854. Optionally, a core wrap 840 can be placed on top of the absorbent composite 812.

Figure 8:
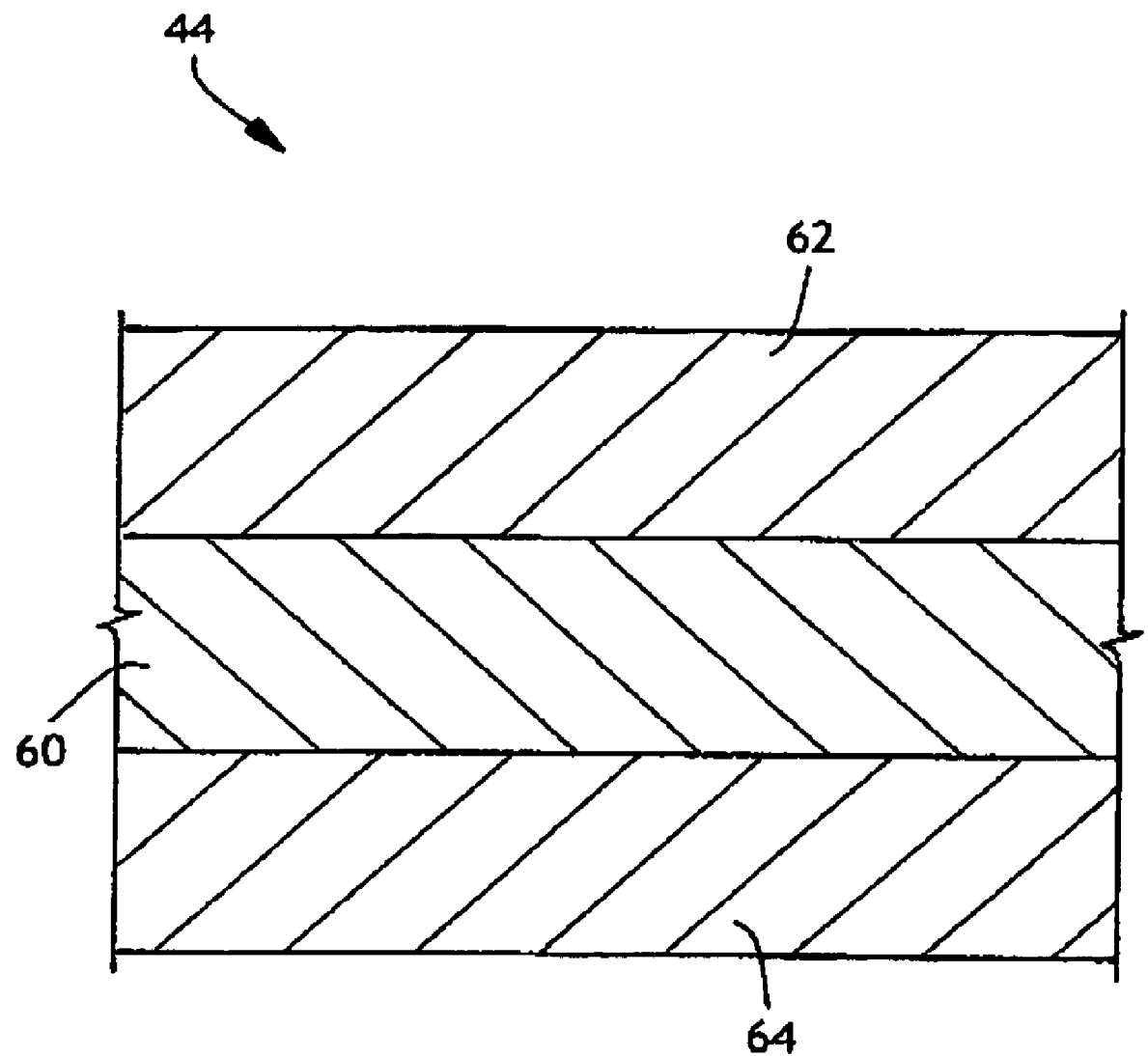
FIG. 8 is a cross-sectional side view of a layered absorbent core according to the present invention.

In general, the absorbent composite 44 is often a unitary structure comprising a substantially uniform distribution of superabsorbent, fibers, and any other optional additives. However, referring to FIG. 8, in some aspects, the absorbent composite 44 may be further enhanced through structural modifications when combined with the superabsorbent fibers of the present invention. For example, providing a layer 65 comprising substantially superabsorbent polymer particles sandwiched between layers 67 and 64 comprising substantially superabsorbent fibers of the present invention can result in an absorbent composite 44 having improved absorbent properties, such as fluid insult intake rate, when compared to a structure comprising a substantially uniform distribution of the superabsorbent polymer particles and fluff fibers. Such layering can occur in the z-direction of the absorbent composite 44 and may optionally cover the entire x-y area. However, the layers 65 and 64 need not be discreet from one another. For example, in some aspects, the z-directional middle portion 65 of the absorbent composite need only contain a higher superabsorbent polymer particles percentage (e.g., at least about 10% by weight higher) than the top layer 67 and/or bottom layer 64 of the absorbent composite 44. Desirably, the layers 65 and 64 are present in the area of the absorbent composite 44 that is within an insult target zone.

As referenced above, the absorbent composite 44 includes absorbent material, such as superabsorbent material. Accordingly, the absorbent composite 44 can comprise a quantity of superabsorbent fibers of the present invention, superabsorbent polymer particles and/or fluff contained within a matrix of fibers. In some aspects, the total amount of superabsorbent fibers of the present invention in the absorbent composite 44 can be at least about 10 wt % of the composite, such as at least about 30 wt %, or at least about 60 wt % or at least about 90 wt %, or between about 10 wt % and about 100 wt % of the composite, or between about 30 wt % to about 90 wt % by weight of the composite to provide improved benefits. Optionally, the amount of superabsorbent fibers can be at least about 95 wt % of the composite. In other aspects, the absorbent composite 44 can comprise about 35 wt % or less fluff, such as about 20 wt % or less, or 10 wt % or less fluff.

It should be understood that the present invention is not restricted to use with superabsorbent fibers of the present invention, superabsorbent polymer particles and/or fluff. In some aspects, the absorbent composite 44 may additionally or alternatively include materials such as surfactants, ion exchange resin particles, moisturizers, emollients, perfumes, natural fibers, synthetic fibers, fluid modifiers, odor control additives, and combinations thereof. Alternatively, the absorbent composite 44 can include a foam.

In order to function well, the absorbent composite 44 can have certain desired properties to provide improved performance as well as greater comfort and confidence among the user. For instance, the absorbent composite 44 can have corresponding configurations of absorbent capacities, densities, basis weights and/or sizes which are selectively constructed and arranged to provide desired combinations of absorbency properties such as liquid intake rate, absorbent capacity, liquid distribution or fit properties such as shape maintenance and aesthetics. Likewise, the components can have desired wet to dry strength ratios, mean flow pore sizes, permeabilities and elongation values.

As mentioned above, the absorbent composite 44 can optionally include elastomeric polymer fibers. The elastomeric material of the polymer fibers may include an olefin elastomer or a non-olefin elastomer, as desired. For example, the elastomeric fibers can include olefinic copolymers, polyethylene elastomers, polypropylene elastomers, polyester elastomers, polyisoprene, cross-linked polybutadiene, diblock, triblock, tetrablock, or other multi-block thermoplastic elastomeric and/or flexible copolymers such as block copolymers including hydrogenated butadiene-isoprene-butadiene block copolymers; stereoblock polypropylenes; graft copolymers, including ethylene-propylene-diene terpolymer or ethylene-propylene-diene monomer (EPDM) rubber, ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Inc. under the trade designation KRATON elastomeric resin or from Dexco, a division of ExxonMobil Chemical Company under the trade designation VECTOR (SIS and SBS polymers); blends of thermoplastic elastomers with dynamic vulcanized elastomer-thermoplastic blends; thermoplastic polyether ester elastomers; ionomeric thermoplastic elastomers; thermoplastic elastic polyurethanes, including those available from Invista Corporation under the trade name LYCRA polyurethane, and ESTANE available from Noveon, Inc., a business having offices located in Cleveland, Ohio U.S.A.; thermoplastic elastic polyamides, including polyether block amides available from AtoFina Chemicals, Inc. (a business having offices located in Philadelphia, Pa. U.S.A.) under the trade name PEBAX; polyether block amide; thermoplastic elastic polyesters, including those available from E. I. Du Pont de Nemours Co., under the trade name HYTREL, and ARNITEL from DSM Engineering Plastics (a business having offices located in Evansville, Ind., U.S.A.) and single-site or metallocene-catalyzed polyolefins having a density of less than about 0.89 grams/cubic centimeter, available from Dow Chemical Co. (a business having offices located in Freeport, Tex. U.S.A.) under the trade name AFFINITY; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS and SEPS. In these copolymers the A blocks are polystyrene and the B blocks are a rubbery component. Generally, these triblock copolymers have molecular weights that can vary from the low thousands to hundreds of thousands, and the styrene content can range from 5% to 75% based on the weight of the triblock copolymer. A diblock copolymer is similar to the triblock, but is of an AB structure. Suitable diblocks include styrene-isoprene diblocks, which have a molecular weight of approximately one-half of the triblock molecular weight having the same ratio of A blocks to B blocks.

In desired arrangements, the polymer fibers can include at least one material selected from the group consisting of styrenic block copolymers, elastic polyolefin polymers and co-polymers and EVA/EMA type polymers.

In some particular arrangements, for example, the elastomeric material of the polymer fibers can include various commercial grades of low crystallinity, lower molecular weight metallocene polyolefins, available from ExxonMobil Chemical Company (a company having offices located in Houston, Tex., U.S.A.) under the VISTAMAXX trade designation. Some VISTAMAXX materials are believed to be metallocene propylene ethylene co-polymer. For example, in one aspect the elastomeric polymer can be VISTAMAXX PLTD 2210. In other aspects, the elastomeric polymer can be VISTAMAXX PLTD 1778. In a particular aspect, the elastomeric polymer is VISTAMAXX 2370. Another optional elastomeric polymer is KRATON blend G 2755 from Kraton Inc. The KRATON material is believed to be a blend of styrene ethylene-butylene styrene polymer, ethylene waxes and tackifying resins.

In some aspects, the elastomeric polymer fibers can be produced from a polymer material having a selected melt flow rate (MFR). In a particular aspect, the MFR can be up to a maximum of about 300. Alternatively, the MFR can be up to about 230 or 250. In another aspect, the MFR can be a minimum of not less than about 9, or not less than 20. The MFR can alternatively be not less than about 50 to provide desired performance. The described melt flow rate has the units of grams flow per 10 minutes (g/10 min). The parameter of melt flow rate is well known, and can be determined by conventional techniques, such as by employing test ASTM D 1238 70 "extrusion plastometer" Standard Condition "L" at 230° C. and 2.16 kg applied force.

As referenced above, the elastomeric polymer fibers of the absorbent composite 44 can include an amount of a surfactant. The surfactant can be combined with the elastomeric polymer fibers of the absorbent composite in any operative manner. Various techniques for combining the surfactant are conventional and well known to persons skilled in the art. For example, the surfactant may be compounded with the elastomeric polymer employed to form a meltblown fiber structure. In a particular feature, the surfactant may be configured to operatively migrate or segregate to the outer surface of the fibers upon the cooling of the fibers. Alternatively, the surfactant may be applied to or otherwise combined with the elastomeric polymer fibers after the fibers have been formed.

The elastomeric polymer fibers can include an operative amount of surfactant, based on the total weight of the fibers and surfactant. In some aspects, the elastomeric polymer fibers can include at least a minimum of about 0.1% by weight surfactant, as determined by water extraction. The amount of surfactant can alternatively be at least about 0.15% by weight, and can optionally be at least about 0.2% by weight to provide desired benefits. In other aspects, the amount of surfactant can be generally not more than a maximum of about 2% by weight, such as not more than about 1% by weight, or not more than about 0.5% by weight to provide improved performance.

If the amount of surfactant is outside the desired ranges, various disadvantages can occur. For example, an excessively low amount of surfactant may not allow fibers, such as hydrophobic meltblown fibers, to wet with the absorbed fluid. In contrast, an excessively high amount of surfactant may allow the surfactant to wash off from the fibers and undesirably interfere with the ability of the absorbent composite to transport fluid, or may adversely affect the attachment strength of the absorbent composite to the absorbent article. Where the surfactant is compounded or otherwise internally added to the polymer fibers, an excessively high level of surfactant can create conditions that cause poor formation of the polymer fibers and interfiber bonds.

In some configurations, the surfactant can include at least one material selected from the group that includes polyethylene glycol ester condensates and alkyl glycoside surfactants. For example, the surfactant can be a GLUCOPON surfactant, available from Cognis Corporation, which can be composed of 40 wt % water, and 60 wt. % d-glucose, decyl, octyl ethers and oligomerics.

In other aspects of the invention, the surfactant can be in the form of a sprayed-on surfactant comprising a water/surfactant solution which includes 16 liters of hot water (about 45° C. to 50° C.) mixed with 0.20 kg of GLUCOPON 220 UP surfactant available from Cognis Corporation and 0.36 kg of AHCHOVEL Base N-62 surfactant available from Uniqema. When employing a sprayed-on surfactant, a relatively lower amount of sprayed-on surfactant may be desirable to provide the desired containment of the superabsorbent polymer particles. Excessive amounts of the fluid surfactant may hinder the desired attachment of the superabsorbent polymer particles to the molten, elastomeric meltblown fibers, for example.

An example of an internal surfactant or wetting agent that can be compounded with the elastomeric fiber polymer can include a MAPEG DO 400 PEG (polyethylene glycol) ester, available from BASF (a business having offices located in Freeport, Tex., U.S.A.). Other internal surfactants can include a polyether, a fatty acid ester, a soap or the like, as well as combinations thereof.

As referenced above, the absorbent composite 44 can optionally include fluff, such as cellulosic fibers. Such cellulosic fibers may include, but are not limited to, chemical wood pulps such as sulfite and sulfate (sometimes called Kraft) pulps, as well as mechanical pulps such as ground wood, thermomechanical pulp and chemithermomechanical pulp. More particularly, the pulp fibers may include cotton, other typical wood pulps, cellulose acetate, debonded chemical wood pulp, and combinations thereof. Pulps derived from both deciduous and coniferous trees can be used. Additionally, the cellulosic fibers may include such hydrophilic materials as natural plant fibers, milkweed floss, cotton fibers, microcrystalline cellulose, microfibrillated cellulose, or any of these materials in combination with wood pulp fibers. Suitable cellulosic fluff fibers can include, for example, NB480 (available from Weyerhaeuser Co.); NB416, a bleached southern softwood Kraft pulp (available from Weyerhaeuser Co.); CR 54, a bleached southern softwood Kraft pulp (available from Bowater Inc., a business having offices located in Greenville, S.C. U.S.A).; SULPHATATE HJ, a chemically modified hardwood pulp (available from Rayonier Inc., a business having offices located in Jesup, Ga. U.S.A.); NF 405, a chemically treated bleached southern softwood Kraft pulp (available from Weyerhaeuser Co.); and CR 1654, a mixed bleached southern softwood and hardwood Kraft pulp (available from Bowater Inc.) As referenced above, the absorbent composite 44 can optionally include a desired amount of superabsorbent polymer particles (SAPs). SAP particles typically are polymers of unsaturated carboxylic acids or derivatives thereof. These polymers are rendered water insoluble, but water swellable, by crosslinking the polymer with a di- or polyfunctional internal crosslinking agent. These internally crosslinked polymers are at least partially neutralized and contain pendant anionic carboxyl groups on the polymer backbone that enable the polymer to absorb aqueous fluids, such as body fluids. Typically, the SAP particles are subjected to a post-treatment to crosslink the pendant anionic carboxyl groups on the surface of the particle.

The superabsorbent particles can be selected from natural, synthetic and modified natural polymers and materials. The superabsorbent particles can be inorganic materials, such as silica gels, or organic compounds, such as crosslinked polymers. The term "crosslinked" refers to any means for effectively rendering normally water-soluble materials substantially water insoluble, but swellable. Such means can comprise, for example, physical entanglement, crystalline domains, covalent bonds, ionic complexes and associations, hydrophilic associations, such as hydrogen bonding, and hydrophobic associations or Van der Waals forces. Processes for preparing synthetic, absorbent gelling polymers are disclosed in U.S. Pat. No. 4,076,663, issued to Masuda et al., and U.S. Pat. No. 4,286,082, issued to Tsubakimoto et al., all of which are incorporated herein by reference in a manner that is consistent herewith. Suitable superabsorbent particles are available from various commercial vendors, such as Stockhausen, Inc., BASF Inc. and others. In one example, the superabsorbent material was SR 1642, available from Stockhausen, Inc., a business having offices located in Greensboro, N.C., U.S.A.

The absorbent article of the present invention includes superabsorbent fibers of the present invention. In some aspects, the present invention provides substantially water-insoluble, water-swellable, non-regenerated, carboxyalkyl cellulose fibers. The fibers have a surface having the appearance of the surface of a cellulose fiber and include a plurality of non-permanent intra-fiber metal crosslinks and a plurality of permanent intra-fiber metal crosslinks. Thus, the fibers of the invention have irregular surface patterns (including striations, pits, and pores) coextensive with the fibers' surface. The carboxyalkyl cellulose fibers of the invention are fibers having superabsorbent properties. The superabsorbent fibers are water-swellable, water-insoluble fibers that substantially retain a fibrous structure in their expanded, water-swelled state.

The superabsorbent fibers of the invention are cellulosic fibers that have been modified by carboxyalkylation and crosslinking. Water swellability imparted to the fibers through carboxyalkylation and crosslinking renders the fibers substantially insoluble in water. The fibers have a degree of carboxyl group substitution effective to provide advantageous water swellability. The fibers are crosslinked to an extent sufficient to render the fiber water insoluble. The superabsorbent fibers have a liquid absorption capacity that is increased compared to unmodified fluff pulp fibers.

The superabsorbent fibers of the invention are substantially insoluble in water. As used herein, fibers are considered to be water soluble when they substantially dissolve in excess water to form a solution, losing their fiber form and becoming essentially evenly dispersed throughout the water solution. Sufficiently carboxyalkylated cellulosic fibers that are free from a substantial degree of crosslinking will be water soluble, whereas the fibers of the invention, carboxyalkylated and crosslinked fibers, are substantially water insoluble.

The superabsorbent fibers of the invention are substantially water-insoluble, water-swellable fibers. As used herein, the term "substantially water-insoluble, water-swellable" refers to fibers that, when exposed to an excess of an aqueous medium (e.g., bodily fluids such as urine or blood, water, synthetic urine, or 0.9 weight percent solution of sodium chloride in water), swell to an equilibrium volume, but do not dissolve into solution.

Figure 9A:
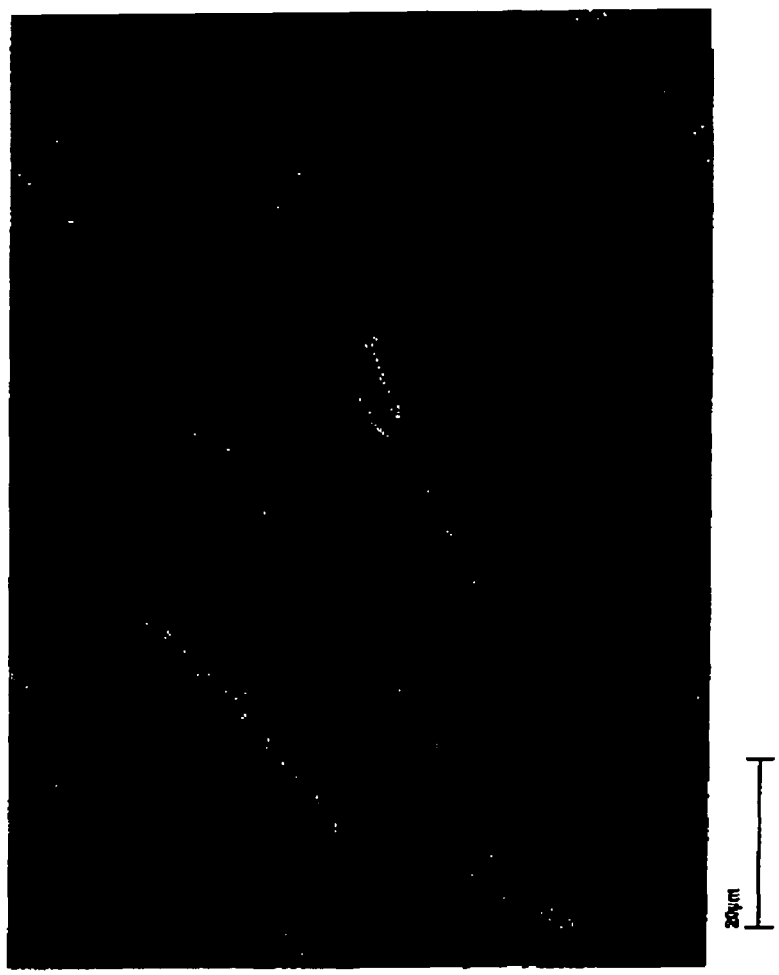
FIG. 9A is a scanning electron microscope photograph (1000×) of cellulose fibers useful for making the representative crosslinked carboxymethyl cellulose fibers of the invention.
Figure 9B:
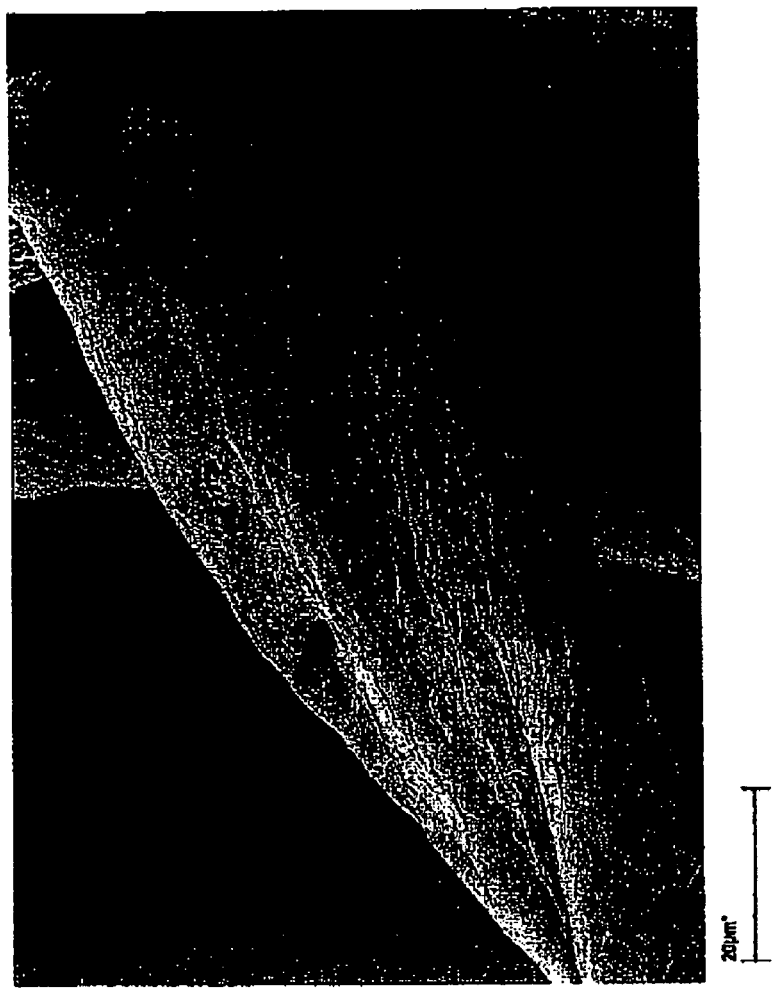
FIG. 9B is a scanning electron microscope photograph (1000×) of representative crosslinked carboxymethyl cellulose fibers of the invention.
Figure 9C:
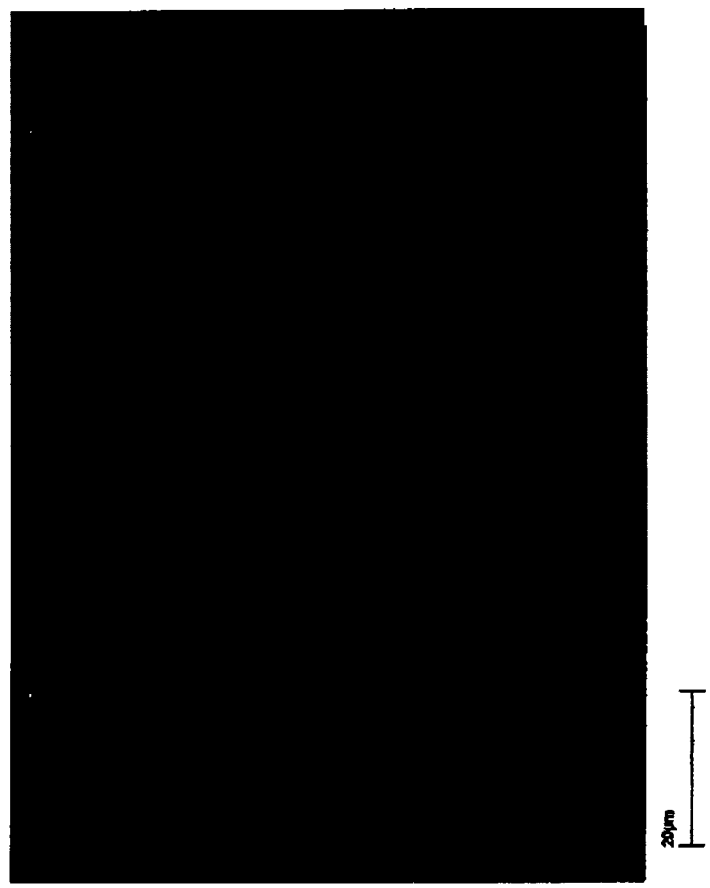
FIG. 9C is a scanning electron microscope photograph (1000×) of regenerated cellulose fibers.

The water-swellable, water-insoluble fibers of the invention have a surface having the appearance of the surface of a cellulose fiber. Like native fibers, the superabsorbent fibers of the present invention have a surface that includes striations, pits, and pores. The superabsorbent fibers of the invention retain the surface structure of cellulose fibers because the fibers of the invention are prepared by methods that do not include dissolving the fibers into solution and then regenerating those fibers from the solution. Fibers that are prepared by regeneration from solution substantially lack typical fiber structures present in native fibers. Regenerated fibers lack, among other structural features, surface structure (e.g., striations, pits, and pores). FIGS. 9A, 9B, and 9C are photomicrographs comparing the surfaces of representative wood pulp fibers, representative superabsorbent fibers of the invention (prepared from the wood pulp fibers shown in FIG. 9A), and representative regenerated fibers, respectively. Referring to FIGS. 9A and 9B, the surfaces of representative wood pulp fibers and representative superabsorbent fibers of the invention are shown to include features (e.g., irregular surface patterns coextensive with the fibers' surface). In contrast, the surface of representative regenerated fibers substantially lack such surface structure (see FIG. 9C).

As used herein, the term "regenerated fiber" refers to a fiber that has been prepared by regeneration (i.e., return to solid form) from a solution that includes dissolved fiber. The term "non-regenerated" refers to a fiber that has not been dissolved into solution and then regenerated (i.e., returned to solid form) from that solution. As noted above, whereas the non-regenerated fibers of the invention substantially retain the surface structure of the cellulose fibers from which they are made, regenerated fibers do not.

In some aspects, the superabsorbent fibers of the invention can include non-permanent intra-fiber crosslinks. The non-permanent intra-fiber crosslink is a metal-carboxyl crosslink formed using a multi-valent metal ion. The non-permanent crosslinks can unform and reform in use (e.g., dissociate and re-associate on liquid insult in an absorbent article). In some aspects, the fibers of the invention further include permanent intra-fiber crosslinks. Permanent intra-fiber crosslinks are stable in use and do not dissociate and re-associate on liquid insult in an absorbent article.

The superabsorbent fibers of the invention are substantially insoluble in water while being capable of absorbing water. In some aspects, the superabsorbent fibers are rendered water insoluble by virtue of a plurality of non-permanent intra-fiber metal crosslinks. As used herein, the term "non-permanent intra-fiber metal crosslinks" refers to the nature of the crosslinking that occurs within individual fibers of the invention (i.e., intra-fiber) and among and between each fiber's constituent carboxyalkyl cellulose polymers.

In some aspects, the superabsorbent fibers of the present invention are intra-fiber crosslinked with a metal crosslink. The metal crosslink arises as a consequence of an associative interaction (e.g., bonding) between functional groups on the fiber's carboxyalkyl cellulose polymers (e.g., carboxy, carboxylate, or hydroxyl groups) and a multi-valent metal species. Suitable multi-valent metal species include metal ions having a valency of two or greater and that are capable of forming an associative interaction with a carboxyalkyl cellulose polymer (e.g., reactive toward associative interaction with the polymer's carboxy, carboxylate, or hydroxyl groups). The carboxyalkyl cellulose polymers are crosslinked when the multi-valent metal species forms an associative interaction with functional groups on the carboxyalkyl cellulose polymer. A crosslink may be formed within a carboxyalkyl cellulose polymer or may be formed between two or more carboxyalkyl cellulose polymers within a fiber. The extent of crosslinking affects the water solubility of the fibers and the ability of the fiber to swell on contact with an aqueous liquid (i.e., the greater the crosslinking, the greater the insolubility).

In some aspects, the fibers of the invention include non-permanent intra-fiber metal crosslinks. As used herein, the term "non-permanent" refers to the metal-carboxyl cellulose crosslink. It is generally understood that the crosslinks of typical crosslinked cellulose fibers are generally permanent in nature (i.e., crosslinks that are stable to ordinary use conditions, such as cellulose wetting on liquid insult occurring in an absorbent article). Permanent crosslinks are those that do not dissociate during the fibers' use and are typically covalent crosslinks derived from reaction of an organic compound having at least two functional groups capable of reacting with at least one functional group of a cellulose polymer (e.g., a diether crosslink derived from crosslinking cellulose with a dihalide such as 1,3-dichloro-2-propanol, or a diester crosslink derived from crosslinking cellulose with citric acid). In contrast, a non-permanent crosslink is a crosslink that provides a crosslink within or between a fiber's carboxyalkyl cellulose polymers, but is reactive toward liquid insult. The non-permanent crosslinks of the fibers of the present invention can be unformed and reformed on liquid insult. The metal crosslinks of the fibers of the invention have the characteristic of dissociation on liquid insult, which allow the fibers to expand and swell during liquid acquisition. Once liquid acquisition is complete (i.e., insult terminated), re-association between the dissociated multi-valent metal ion species and the carboxyalkyl cellulose polymer occurs to re-establish a crosslink. In such an instance, the new crosslink is formed in fibers now swollen with acquired liquid. It will be appreciated that the process of dissociating and re-associating (breaking and reforming crosslinks) the multi-valent metal ion and carboxyalkyl cellulose polymer is dynamic and also occurs during liquid acquisition. In some aspects, by virtue of the non-permanent crosslinks, the fibers of the invention have the unique property of maintaining structural integrity while swelling on liquid insult.

In some aspects, the superabsorbent fibers of the present invention include non-permanent intra-fiber metal crosslinks. The metal crosslinks include multi-valent metal ion crosslinks that include one or more metal ions selected from aluminum, boron, bismuth, cerium, chromium, titanium, zirconium, and mixtures thereof. In one particular aspect, the crosslinks are formed through the use of an aluminum crosslinking agent. Suitable aluminum crosslinking agents include aluminum acetates, aluminum sulfate, aluminum chloride, and aluminum lactate. Representative aluminum acetates include aluminum monoacetate, aluminum diacetate, aluminum triacetate, aluminum hemiacetate, aluminum subacetate, and mixtures of aluminum acetates made from non-stoichiometric amounts of acetate and hydroxide in an organic solvent that is water miscible. In one aspect, the aluminum crosslinking agent is aluminum monoacetate stabilized with boric acid (aluminum acetate, basic, containing boric acid as a stabilizer, $CH_3CO_2Al(OH)_2 \cdot \frac{1}{3}H_3BO_3$, Aldrich Chemical Co.). In another aspect, the aluminum crosslinking agent is prepared immediately prior to use (see Examples 4 and 5).

In some aspects, the superabsorbent fibers of the present invention also include permanent crosslinks. In this aspect, the fibers include non-permanent metal ion intra-fiber crosslinks and permanent intra-fiber crosslinks. Permanent intra-fiber crosslinks are crosslinks that are stable in use (e.g., stable to liquid insult when in use in an absorbent article, such as a training pant for example). Permanent intra-fiber crosslinks can be made by crosslinking the fibers with an organic compound having at least two functional groups capable of reacting with at least one functional group selected from carboxyl, carboxylic acid, or hydroxyl groups. Permanent intra-fiber crosslinks include ether, amide, and ester crosslinks (e.g., diether crosslinks).

Permanent crosslinks can be incorporated into the fibers of the invention in several ways: 1) prior to carboxyalkylation; 2) at the same time as carboxyalkylation; 3) after carboxyalkylation and before treating with a multi-valent metal ion crosslinking agent; or 4) after treating with a multi-valent metal ion crosslinking agent. Permanent crosslinking agents can be either reactive or latent. Reactive permanent crosslinking agents form crosslinks: 1) prior to carboxyalkylation; 2) at the same time as carboxyalkylation; or 3) after carboxyalkylation and before treating with a multi-valent metal ion crosslinking agent. Latent crosslinking agents are not reactive in the presence of water and can be incorporated into the fiber: 1) prior to carboxyalkylation; 2) at the same time as carboxyalkylation; 3) after carboxyalkylation and before treating with a multi-valent metal ion crosslinking agent; or 4) after treating with a multi-valent metal ion crosslinking agent. The latent crosslinking agents are capable of reacting to the functional groups on the carboxyalkyl cellulose fibers in a later stage when the carboxyalkyl cellulose fibers are completely dry and suitable conditions, such as high temperature (e.g. greater than about 80° C.), are provided.

In some aspects, crosslinked carboxyalkyl cellulose fibers of the present invention can be made from crosslinked pulp fibers. The crosslinks of the crosslinked cellulose fibers useful in making the carboxyalkyl cellulose are crosslinks that are stable (i.e., permanent) to the carboxyalkylation reaction conditions. A method for making crosslinked carboxyalkyl cellulose fibers from crosslinked fibers and subsequent crosslinking to incorporate non-permanent crosslinks is described in Example 6. Example 6 describes aluminum acetate crosslinked carboxyalkyl cellulose made from 1,3-dichloro-2-propanol crosslinked fibers and aluminum acetate crosslinked carboxyalkyl cellulose made from glycerol diglycidal crosslinked fibers.

In one particular aspect, crosslinked carboxyalkyl cellulose fibers of the present invention can be made by treating cellulose fibers with a crosslinking agent that provides permanent crosslinks and a carboxyalkylating agent during carboxyalkylation. A method for making crosslinked carboxyalkyl cellulose fibers by treating fibers with a crosslinking agent and a carboxyalkylating agent during carboxyalkylation and subsequent crosslinking to incorporate non-permanent crosslinks is described in Example 7. Example 7 describes treating cellulose fibers with 1,3-dichloro-2-propanol, sodium hydroxide and sodium monochloroacetate to provide carboxymethyl cellulose having permanent crosslinks followed by crosslinking with aluminum chloride to incorporate non-permanent crosslinks.

Suitable crosslinking agents useful in making ether crosslinks include dihalide crosslinking agents, such as 1,3-dichloro-2-propanol; diepoxide crosslinking agents, such as vinylcyclohexene dioxide, butadiene dioxide, and diglycidyl ethers (e.g., glycerol diglycidal, 1,4-butanediol diglycidal, and poly(ethylene glycol diglycidal)); sulfone compounds such as divinyl sulfone; bis(2-hydroxyethyl)sulfone, bis(2-chloroethyl)sulfone, and disodium tris(β-sulfatoethyl)sulfonium inner salt; and diisocyanates.

Other suitable crosslinking agents useful for making permanent crosslinks include urea-based formaldehyde addition products (e.g., N-methylol compounds), polycarboxylic acids and polyamines.

Suitable urea-based crosslinking agents include methylolated ureas, methylolated cyclic ureas, methylolated lower alkyl substituted cyclic ureas, methylolated dihydroxy cyclic ureas, dihydroxy cyclic ureas, and lower alkyl substituted cyclic ureas. Specific preferred urea-based crosslinking agents include dimethylol urea (DMU, bis[N-hydroxymethyl]urea), dimethylolethylene urea (DMEU, 1,3-dihydroxymethyl-2-imidazolidinone), dimethyldihydroxyethylene urea (DMDHEU, 1,3-dihydroxymethyl-4,5-dihydroxy-2-imidazolidinone), dimethylolpropylene urea (DMPU), dimethylolhydantoin (DMH), dimethyldihydroxy urea (DMDHU), dihydroxyethylene urea (DHEU, 4,5-dihydroxy-2-imidazolidinone), and dimethyldihydroxyethylene urea (DMeDHEU, 4,5-dihydroxy-1,3-dimethyl-2-imidazolidinone).

Polycarboxylic acid crosslinking agents include the use of C2-C9 polycarboxylic acids that contain at least three carboxyl groups (e.g., citric acid and oxydisuccinic acid) as crosslinking agents. Suitable polycarboxylic acid crosslinking agents include citric acid, tartaric acid, malic acid, succinic acid, glutaric acid, citraconic acid, itaconic acid, tartrate monosuccinic acid, maleic acid, 1,2,3-propane tricarboxylic acid, 1,2,3,4-butanetetracarboxylic acid, all-cis-cyclopentane tetracarboxylic acid, tetrahydrofuran tetracarboxylic acid, 1,2,4,5-benzenetetracarboxylic acid, and benzenehexacarboxylic acid. Other polycarboxylic acids crosslinking agents include polymeric polycarboxylic acids such as poly(acrylic acid), poly(methacrylic acid), poly(maleic acid), poly(methylvinylether-co-maleate) copolymer, poly(methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. Pat. No. 5,998,511, which is incorporated herein by reference in a manner that is consistent herewith.

Suitable crosslinking agents also include crosslinking agents that are reactive toward carboxylic acid groups. Representative organic crosslinking agents include diols and polyols, diamines and polyamines, diepoxides and polyepoxides, polyoxazoline functionalized polymers, and aminols having one or more amino groups and one or more hydroxy groups.

Methods for making the fibers of the invention are described in the Examples below. The absorbent properties of the fibers are also summarized in these examples.

In some aspects, mixtures and/or blends of crosslinking agents can also be used.

The crosslinking agent can include a catalyst to accelerate the bonding reaction between the crosslinking agent and cellulosic fiber. Suitable catalysts include acidic salts, such as ammonium chloride, ammonium sulfate, aluminum chloride, magnesium chloride, and alkali metal salts of phosphorous-containing acids.

Distribution of permanent crosslinks within the carboxyalkyl cellulose fibers can be different depending on when they are incorporated into or onto the fibers. In one aspect, the permanent crosslinking agents are incorporated into the fibers prior to carboxyalkylation or at the same time as carboxyalkylation. Due to the high swelling ratio of the carboxyalkyl cellulose fibers at these stages, the permanent crosslinks are formed throughout the entire intra-fiber structure. In other words, the crosslinks are formed uniformly within the fibers. This type of crosslinking structure is termed "bulk crosslinked" structure. In another aspect, when the permanent crosslinking agents are incorporated onto the fiber surface after carboxyalkylation when the fibers are not at a highly swollen stage, the permanent crosslinks are only formed on the surface of the fibers or have a high concentration of the permanent crosslinks formed on the surface. This type of crosslinking structure is termed "surface crosslinked" structure. In this particular aspect, non-permanent crosslinking agents cannot be incorporated into the fiber prior to carboxyalkylation or at the same time as carboxyalkylation because multi-valent metal ions will interfere with the carboxyalkylation reaction.

The carboxyalkyl cellulose fibers of the invention can be crosslinked by both bulk and surface crosslinks. In one aspect, carboxyalkyl cellulose fibers of the invention can be crosslinked by permanent crosslinks in the bulk and the surface of the fibers. In another aspect, carboxyalkyl cellulose fibers of the invention can be crosslinked by permanent crosslinks in the bulk and non-permanent crosslinks on the surface.

The amount of crosslinking agent applied to the cellulosic fiber will depend on the particular crosslinking agent and is suitably in the range of from about 0.01 to about 10.0 wt % based on the total weight of cellulosic fiber. In some particular aspects, the amount of crosslinking agent applied to the fibers is in the range from about 1.0 to about 8.0 wt % based on the total weight of fibers.

In some aspects, the crosslinking agent can be applied to the cellulosic fibers as an aqueous alcoholic solution. Water is present in the solution in an amount sufficient to swell the fiber to an extent to allow for crosslinking within the fiber's cell wall. However, the solution does not include enough water to dissolve the fiber. Suitable alcohols include those alcohols in which the crosslinking agent is soluble and the fiber to be crosslinked (i.e., unmodified or carboxyalkylated cellulosic fiber) is not. Representative alcohols include alcohols that include from 1 to 5 carbon atoms, for example, methanol, ethanol, n-propanol, isopropanol, n-butanol, isobutanol, s-butanol, and pentanols. In one particular aspect, the alcohol is ethanol. In another particular aspect, the alcohol is methanol.

It will be appreciated that due to their fibers' structure, the fibers of the invention can have a distribution of carboxyl and/or crosslinking groups along the fiber's length and through the fiber's cell wall. Generally, there can be greater carboxyalkylation and/or crosslinking on or near the fiber surface than at or near the fiber core. Surface crosslinking may be advantageous to improve fiber dryness and provide a better balance of total absorbent capacity and surface dryness. Fiber swelling and soak time can also affect the carboxyalkylation and crosslinking gradients. Such gradients may be due to the fiber structure and can be adjusted and optimized through control of carboxyalkylation and/or crosslinking reaction conditions.

The substantially water-insoluble, water-swellable, non-regenerated, carboxyalkyl cellulose fibers of the present invention are absorbent fibers and may be used in a variety of applications. For example, the fibers of the invention can be incorporated into absorbent articles (e.g., infant diapers, adult incontinence products, and feminine care products).

Cellulosic fibers are a starting material for preparing the superabsorbent fibers of the invention. Although available from other sources, suitable cellulosic fibers are derived primarily from wood pulp. Suitable wood pulp fibers for use with the invention can be obtained from well-known chemical processes such as the Kraft and sulfite processes, with or without subsequent bleaching. Pulp fibers can also be processed by thermomechanical, chemithermomechanical methods, or combinations thereof. A high alpha cellulose pulp is also a suitable wood pulp fiber. A suitable pulp fiber is produced by chemical methods. However, groundwood fibers, recycled or secondary wood pulp fibers, and bleached and unbleached wood pulp fibers can also be used. Suitable fibers can include hardwood and/or softwood fibers. Suitable fibers are commercially available from a number of companies, including Weyerhaeuser Company. For example, suitable cellulosic fibers produced from southern pine that are usable with the present invention are available from Weyerhaeuser Company under the designations CF416, NF405, PL416, FR516, and NB416. Other suitable fibers include northern softwood and eucalyptus fibers. Suitable non-wood fibers include rye grass fibers and cotton linters.

Cellulosic fibers having a wide range of degree of polymerization are suitable for forming the fiber of the invention. In some aspects, the cellulosic fiber has a relatively high degree of polymerization, greater than about 1000, such as about 1500 to about 3000, or about 1500 to about 2500. Higher DP cellulosic fibers can be a desirable starting material for the invention because they generally yield crosslinked carboxyalkyl cellulose fiber with higher absorbent capacity.

In some aspects, the fibers have an average length greater than about 1.0 mm. Consequently, the fibers are suitably prepared from fibers having lengths greater than about 1.0 mm. In some particular aspects, fibers having lengths suitable for preparing the fibers can include southern pine, northern softwood, and eucalyptus fibers, the average length of which is about 2.8 mm, about 2.0 mm, and about 1.0 mm, respectively.

In some aspects, the fibers of the invention are carboxyalkylated cellulosic fibers. As used herein, "carboxyalkylated cellulosic fibers" refer to cellulosic fibers that have been carboxyalkylated by reaction of cellulosic fibers with a carboxyalkylating agent. It will be appreciated that the term "carboxyalkylated cellulosic fibers" includes free acid and salt forms of the carboxyalkylated fibers. Suitable metal salts include sodium, potassium, and lithium salt, among others. Carboxyalkylated cellulosic fibers can be produced by reacting a hydroxyl group of the cellulosic fiber with a carboxyalkylating agent to provide a carboxyalkyl cellulose.

Suitable carboxyalkylating agents include monochloroacetic acid and its salts, 3-chloropropionic acid and its salts, and acrylamide. The carboxyalkyl celluloses useful in preparing the fibers of the invention include carboxymethyl celluloses, carboxyethyl celluloses and carboxymethyl ethyl celluloses.

The fibers of the invention can be characterized as having an average degree of carboxyl group substitution of from about 0.5 to about 1.5. In some aspects, the fibers have an average degree of carboxyl group substitution of from about 0.7 to about 1.2. In other aspects, the fibers have an average degree of carboxyl group substitution of from about 0.8 to about 1.0. As used herein, the "average degree of carboxyl group substitution" refers to the average number of moles of carboxyl groups per mole of glucose unit in the fiber. It will be appreciated that the fibers of the present invention include a distribution of carboxyl functional groups having an average degree of carboxyl substitution as, noted above.

As referenced above, the fibers of the invention can exhibit superabsorbent properties. The fibers of the invention have a liquid absorbent capacity of at least about 10 grams/gram (g/g), as measured by the Centrifuge Retention Capacity (CRC) Test described above. In one aspect, the fibers have a capacity of at least about 20 g/g. In another aspect, the fibers have a capacity of at least about 25 g/g. In yet another aspect the fibers have a capacity from about 10 to about 40 g/g.

The fibers of the invention have a liquid absorbent capacity of from about 30 to about 70 g/g as measured by the Free Swell Capacity Test described below. In one aspect, the fibers have a capacity of at least about 50 g/g. In another aspect, the fibers have a capacity of at least about 60 g/g.

The fibers of the invention have a liquid absorbent capacity of from about 10 to about 40 g/g as measured by the absorbency under load (AUL) test described below. In one aspect, the fibers have a capacity of at least about 20 g/g. In another aspect, the fibers have a capacity of at least about 30 g/g.

The fibers of the invention can be formed into pads by, for example, conventional air-laying techniques and the performance characteristics of those pads determined. An advantageous property of the fibers of the invention is that pads formed from these fibers demonstrate rapid liquid acquisition times for multiple insults. For certain pads subjected to multiple insults, liquid acquisition times for subsequent insults actually decreases. The liquid acquisition times for subsequent insults for pads made from fibers of the invention are measured by the Fluid Intake Flowback Evaluation (FIFE) Test described above. The FIFE results for pads formed from the fibers of the invention are presented in the Examples.

In addition to advantageous liquid acquisition, pads formed from the fibers of the invention demonstrate significant strength and integrity after being subject to multiple insults. Pad wet strength results for pads formed from the fibers of the invention are presented in Example 3.

Exemplary methods for making the fibers of the invention are described in Examples 3, 6, and 7. The absorbent properties of the fibers are also summarized in these examples.

In some aspects of the invention, fiber bundles are provided. The fiber bundles are an aggregate (or plurality) of the fibers of the invention described above. In the fiber bundles, adjacent fibers are in contact with each other. The bundle is an aggregate of the fibers in which contact between adjacent fibers is maintained mechanically by, for example, friction or entanglement; or chemically by, for example, hydrogen bonding or crosslinking.

The fiber bundle can have a diameter of from about 50 to about 2000 μm, a basis weight of from about 200 to about 2000 g/m$^2$, and a density of from about 0.03 to about 1.5 g/cm$^3$.

Like their component fibers, the fiber bundles of the invention exhibit significant absorbent capacity.

In some aspects, the present invention provides methods for making substantially water-insoluble, water-swellable, non-regenerated, carboxyalkyl cellulose fibers, wherein the fibers have a surface having the appearance of the surface of a cellulose fiber, and wherein the fibers include a plurality of non-permanent intra-fiber metal crosslinks and a plurality of permanent intra-fiber crosslinks. Methods for making fiber bundles including the fibers are also provided.

The fibers of the invention can be prepared by a method that includes carboxylating and crosslinking cellulose fibers. In some aspects, cellulosic fibers are carboxyalkylated and then crosslinked. In this method, carboxyalkylated cellulosic fibers are treated with an amount of crosslinking agent sufficient to render the resulting fibers substantially insoluble in water.

In other aspects, cellulosic fibers are crosslinked then carboxyalkylated. In this method, crosslinked cellulosic fibers are carboxyalkylated to render the resulting fibers highly water absorptive. The fibers formed by either method are highly water absorptive, water swellable, and water insoluble.

In some aspects, the method includes carboxyalkylating cellulose fibers by treating cellulose fibers with a carboxyalkylating agent and a crosslinking agent or agents. In this method, the carboxyalkyl cellulose fibers are not dissolved and therefore retain their fibrous form throughout the method steps.

In some aspects, the method includes carboxyalkylating cellulose fibers by treating cellulose fibers with a carboxyalkylating agent in a carboxyalkylating medium to provide carboxyalkyl cellulose fibers; and treating the carboxyalkyl cellulose fibers with a multi-valent metal ion crosslinking agent and a second crosslinking agent to provide substantially water-insoluble, water-swellable, carboxyalkyl cellulose fibers In some aspects, a second crosslinking agent is utilized to provide substantially water-insoluble, water-swellable, carboxyalkyl cellulose fibers, wherein the second crosslinking agent imparts permanent crosslinks to the fibers, and wherein the fibers retain their fibrous form throughout the method. In some particular aspects, the fibers are treated with a metal ion crosslinking agent before treating the fibers with the second crosslinking agent. In other particular aspects, the fibers are treated with the metal ion crosslinking agent after treating the fibers with the second crosslinking agent. In yet other aspects, the fibers are treated with the metal ion crosslinking agent and the second crosslinking agent at the same time. In some aspects, the second crosslinking agent is 1,3-dichloro-2-propanol. In other aspects, the multi-valent metal ion crosslinking agent comprises an aluminum compound.

In some aspects, the method for making substantially water-insoluble, water-swellable, carboxyalkyl cellulose fibers includes treating cellulose fibers with a carboxyalkylating agent and a crosslinking agent that imparts permanent crosslinks to the fibers to provide crosslinked carboxyalkyl cellulose fibers; and treating the crosslinked carboxyalkyl cellulose fibers with a multi-valent metal ion crosslinking agent to provide substantially water-insoluble, water-swellable, carboxyalkyl cellulose fibers, wherein the fibers retain their fibrous form throughout the method. In some particular aspects, the crosslinking agent that imparts permanent crosslinks is 1,3-dichloro-2-propanol. In other particular aspects, the multi-valent metal ion crosslinking agent comprises an aluminum compound.

In some aspects, the method for making substantially water-insoluble, water-swellable, carboxyalkyl cellulose fibers includes treating crosslinked cellulose fibers with a carboxyalkylating agent to the fibers to provide crosslinked carboxyalkyl cellulose fibers; and treating the crosslinked carboxyalkyl cellulose fibers with a multi-valent metal ion crosslinking agent to provide substantially water-insoluble, water-swellable, carboxyalkyl cellulose fibers, wherein the fibers retain their fibrous form throughout the method. In some particular aspects, the crosslinked cellulose fibers are crosslinked with 1,3-dichloro-2-propanol. In other particular aspects, the multi-valent metal ion crosslinking agent comprises an aluminum compound.

In some aspects, the methods further include drying the substantially water-insoluble, water-swellable, carboxyalkyl cellulose fibers. In other aspects, the methods further include fiberizing the substantially water-insoluble, water-swellable, carboxyalkyl cellulose fibers to provide individualized fibers. In yet other aspects, the methods further include fiberizing the substantially water-insoluble, water-swellable, carboxyalkyl cellulose fibers to provide fiber bundles comprising substantially water-insoluble, water-swellable, carboxyalkyl cellulose fibers.

The carboxyalkylating agent can be monochloroacetic acid or its salts, 3-chloropropionic acid or its salts, or acrylamide.

The carboxyalkylating medium comprises a mixture of one or more alcohols and water. In some particular aspects, the alcohol is ethanol. In other particular aspects, the alcohol is isopropanol.

The fibers of the invention include non-permanent intra-fiber crosslinks formed through the use of multi-valent metal ion crosslinking agents. These crosslinking agents include a metal ion selected from aluminum, boron, bismuth, titanium, zirconium, cerium, or chromium ions. Mixtures can also be used. The multi-valent metal ion crosslinking agent is applied in an amount from about 0.1 to about 10 wt % based on the weight of fibers. The amount of crosslinking agent will depend on the nature of the crosslinking agent and the desired absorbent properties in the product fiber.

In some aspects, the multi-valent metal ion crosslinking agent is an aluminum compound. Suitable aluminum crosslinking agents include aluminum acetates, aluminum sulfate, aluminum chloride, and aluminum lactate. Representative aluminum acetates include aluminum monoacetate, aluminum diacetate, aluminum triacetate, aluminum hemiacetate, aluminum subacetate, and mixtures of aluminum acetates made from non-stoichiometric amounts of acetate and hydroxide in an organic solvent that is water miscible. In some particular aspects, the aluminum crosslinking agent is aluminum monoacetate stabilized with boric acid (aluminum acetate, basic, containing boric acid as stabilizer, $CH_3CO_2Al(OH)_2 \cdot 1/3 H_3BO_3$, available from Aldrich Chemical Company). In other particular aspects, the aluminum crosslinking agent is prepared immediately prior to use.

As referenced above, in addition to non-permanent metal ion crosslinks, the fibers of the invention also include permanent intra-fiber crosslinks. Permanent intra-fiber crosslinks can be made by crosslinking the fibers with an organic compound having at least two functional groups capable of reacting with at least one functional group selected from carboxyl, carboxylic acid, or hydroxyl groups. Suitable crosslinking agents for making permanent crosslinks are described above. Representative permanent crosslinks include ether, amide and ester crosslinks.

In some aspects, when cellulose fibers are crosslinked prior to or during carboxyalkylation, suitable crosslinking agents include those that provide permanent crosslinks that are stable to the alkaline conditions of the carboxyalkylation reaction. For these methods, crosslinking agents desirably provide diether crosslinks (e.g., 1,3-dichloro-2-propanol). The permanent crosslinks can be incorporated into the fibers prior to, during, or after carboxyalkylation.

In some aspects, the method includes treating the cellulose fibers with a crosslinking agent prior to carboxyalkylating the cellulose fibers. In this method, crosslinked cellulose fibers are carboxyalkylated. In this aspect, the carboxyalkylated cellulose fibers made from crosslinked fibers are subsequently treated with a multi-valent metal ion crosslinking agent to impart non-permanent crosslinks to the fibers.

In some aspects, the method includes treating the cellulose fibers with a crosslinking agent at the same time as carboxyalkylating the cellulose fibers. In this method, cellulose fibers are crosslinked during carboxyalkylation. In this aspect, the carboxyalkylated, crosslinked cellulose fibers are subsequently treated with a multi-valent metal ion crosslinking agent to impart non-permanent crosslinks to the fibers.

In some aspects, the method includes treating the fibers with a crosslinking agent after carboxyalkylating the cellulose fibers and prior to treating the carboxyalkyl cellulose fibers with a multi-valent metal ion crosslinking agent. In other aspects, the method further includes treating the fibers with a crosslinking agent after treating the carboxyalkyl cellulose fibers with a multi-valent metal ion crosslinking agent.

In some aspects, the multi-valent metal ion crosslinking agent is applied to the fibers in an amount from about 0.1 to about 10 wt % based on the weight of fibers and the crosslinking agent for making permanent crosslinks (e.g., organic compound) is applied to the fibers in an amount from about 0.1 to about 5 wt % based on the weight of fibers. In some particular aspects, the multi-valent metal ion crosslinking agent is applied in an amount from about 1 to about 8 wt % based on the weight of fibers and the crosslinking agent for making permanent crosslinks is applied in an amount of from about 0.5 to about 2 wt % based on the weight of fibers.

The following is a description of one representative method for making the fibers and fiber bundles.

Pulp Preparation

Wood pulp fibers are the starting material for the preparation of the fibers and fiber bundles utilized in the absorbent composite of the present invention. In a representative method, hardwood or softwood chips are cooked in a conventional or modified continuous digester to provide pulp having a Kappa number between 20 and 40. The kraft pulp can then be delignified in an oxygen delignification reactor and then subsequently partially or fully bleached by conventional bleaching processes (e.g., elemental chlorine-free bleaching) and bleaching sequences (DEopD or DEopDED). The pulp capillary viscosity produced by the pulping, delignification, and bleaching steps is greater than about 25 cps and the pulp has a brightness of up to about 87% ISO. The bleached pulp at a consistency of from about 10 to 15% is then dewatered (e.g., press or centrifuge) to provide pulp at a consistency of 30-35%. The dewatered pulp is then further dried to a consistency of 50-60% (i.e., never-dried pulp) or 85-90% (air-dried pulp) by, for example, a through-air dryer. The dry pulp is then ready for carboxyalkyl cellulose formation.

Carboxyalkyl Cellulose Preparation

High consistency pulp (e.g., 50-90%) is introduced into either a batch or a continuous carboxyalkyl cellulose reactor at about room temperature under nitrogen and mixed with alcohol (e.g., isopropanol). The pulp fibers are then treated with 50% by weight sodium hydroxide in water (i.e., mercerization) at about 25° C. for 0.5 to 1 hour. The alkalized pulp is then treated with a carboxyalkylation agent in alcohol (e.g., 50% by weight monochloroacetic acid in ethanol) at a temperature of between about 55-75° C. for three to four hours. During this time the consistency of pulp in the reactor is from about 15% to about 25% with the ratio of alcohol solvent to water less than about 2. Once the carboxyalkylation (i.e., etherization) is complete, the carboxyalkyl cellulose fibers are neutralized by the addition of acid (e.g., 33% by weight hydrogen chloride in water).

In the process, the carboxyalkyl cellulose (e.g., carboxymethyl cellulose, ("CMC")) is produced, having a degree of substitution (DS) of from about 0.5 to about 1.5. The degree of substitution is defined as the moles of carboxyl groups introduced to the fiber per mol of anhydroglucose units. In a continuous process, the alkylization and etherification chemicals are mixed with the pulp in a mixer and the mixture is transported to the reactor without stirring. For a batch process, the chemicals are mixed with the pulp in the reactor with continuous stirring.

As noted above, the carboxyalkyl cellulose preparation includes three stages: (1) alkylization (i.e., mercerization); (2) carboxyalkylation (i.e., etherification); and (3) neutralization and washing.

Representative process conditions for the alkylization stage include a temperature from about 0 to 30° C., a time of about 0.5 to 1.5 hour, a liquor (i.e., alcohol solvent and water) to pulp ratio of from about 2 to about 50, a solvent (ethanol or isopropanol) to water ratio of about 1 to about 10, and a sodium hydroxide charge rate of about 2-4 mol/mol cellulose.

Representative process parameters for the carboxyalkylation reaction stage include a temperature of from about 50° C. to about 80° C., a process time of from about 2 to about 4 hours, a liquor to pulp ratio of from about 2 to about 20, a solvent to water ratio of from about 1 to about 25, and a carboxyalkylating agent (monochloroacetic acid) charge rate of about 1 to 2 mol/mol cellulose.

After neutralization, the carboxyalkylated cellulose fibers are washed (e.g., belt washer or centrifuge) with a mixture of an alcohol (e.g., ethanol) and water (concentration 60-80% mass). In the process, residual salt is less than 5% mass. During the washing step, acetic acid is used to neutralize the carboxyalkyl cellulose fibers.

The carboxyalkyl cellulose fibers so produced are ready for crosslinking.

Crosslinked Carboxyalkyl Cellulose Fiber Preparation

Carboxyalkyl cellulose fibers from the carboxyalkylation reactor are introduced to a continuous reactor at a consistency of about 30%. In the reactor, the carboxyalkyl cellulose fibers are treated with a crosslinking agent at a consistency of about 5-25% at a temperature of from about 20° C. to about 75° C., and for a time of from 0.2 to 2 hours. The temperature and time may depend on the nature of the crosslinking agent. In a representative crosslinking reactor, the liquor (i.e., organic solvent and water) to pulp ratio is from about 2 to 20, the organic solvent to water ratio is from about 1 to about 2, and the crosslinking agent charge rate is from about 2% to about 7% mass based on the weight of carboxyalkyl cellulose fibers.

In some aspects, a crosslinking (permanent crosslinking) reaction is carried out in the carboxyalkyl cellulose reactor where crosslinking (permanent) occurs substantially simultaneously with carboxyalkylation. Crosslinked carboxyalkyl cellulose fibers (having permanent crosslinks) leaving the crosslinking reactor are then subject to solvent removal (e.g., through the use of steam by a steam stripper) to provide substantially solvent-free crosslinked carboxyalkyl cellulose fibers. When the crosslinking agent is applied to the carboxyalkyl cellulose fibers in ethanol, the ethanol stripped from the crosslinked fibers can be returned to an ethanol distillation column for ethanol recovery and recycling.

Ethanol for solvent in the carboxyalkylation reaction can be fed from an ethanol storage tank in liquid communication with an ethanol distillation column for receiving and recycling ethanol from other steps in the process.

Ethanol for the crosslinking step as a solvent for the crosslinking agent can be fed to the crosslinking reactor from ethanol storage.

The substantially ethanol-free fibers can be further defiberized in a fluffer (e.g., pin fluffer or shredder) to provide crosslinked carboxyalkyl cellulose fibers and related crosslinked carboxyalkylated cellulose fiber bundles.

Further Crosslinking of Crosslinked Carboxyalkyl Cellulose Fibers

The substantially ethanol-free crosslinked carboxyalkylated cellulose fibers may be optionally further crosslinked by applying a second crosslinking agent to the crosslinked carboxyalkylated cellulose fibers and then drying the treated crosslinked carboxyalkylated cellulose fibers to provide crosslinked carboxyalkylated cellulose fibers. The optional additional crosslinking occurs during drying, which can be carried out using, for example, fluidized bed dryer, flash dryer, belt conveyor dryer, or drum dryer.

Screening and Packaging Crosslinked Carboxyalkyl Cellulose Fibers

The dried crosslinked carboxyalkyl cellulose fibers and/or fiber bundles can be screened to select particular size distributions. The final fiber and/or fiber bundle product can be sheeted by air-laying processes and the final product packaged in rolls. Alternatively, the fiber and/or fiber bundle products can be baled.

Solvent Recovery, Salt Recovery, and Waste Treatment

The filtrate from the carboxyalkyl cellulose reactor wash and the off gases from the stripper and dryer can be sent to a solvent recovery process. Solvent (e.g., ethanol) can be recovered from the filtrate using a distillation device. Solvent recovered can be recycled to the process. The distillation device residue can be sent to salt recovery process. Residual filtrate can be sent to waste treatment.

The absorbent properties of the crosslinked carboxyalkyl cellulose fibers and fiber bundles can be determined directly or by forming the fibers and/or bundles into pads by air-laying techniques and then testing the pad performance.

Absorbent Composites Comprising the Superabsorbent Fibers

Once the superabsorbent fibers of the present invention have been formed, an absorbent composite can be produced which comprises the superabsorbent fibers. It has been discovered that an absorbent composite comprising up to 100 wt % of the superabsorbent fiber of the present invention and formed by a process which enables formation of interfiber bonds between the superabsorbent fiber (i.e., bonds between two or more fibers) either throughout the absorbent composite (i.e., uniformly or non-uniformly throughout) or only on a surface portion of the absorbent composite can exhibit fluid wicking capability and wet integrity that is better than the same composite that has not been treated, or that is equal to or better than a conventional composite consisting of fluff fiber and superabsorbent particles.

In some aspects, commercially available wood pulp fluff, such as Weyerhaeuser NB 416 (available from Weyerhaeuser Company), was chemically modified through carboxymethylation in an alcohol medium and crosslinked by both internal and surface crosslinking agents, as described above. Suitable fibers are described in U.S. patent application Ser. No. 11/542510 to Qin et al. and U.S. patent application Ser. No. 11/542567 to Qin et al., the content of which are incorporated herein by reference in a manner that is consistent herewith. In one particular aspect, the modified superabsorbent fiber was wet laid in an aqueous alcohol medium. In another particular aspect, the superabsorbent fiber was air-formed and then surface wet treated by a special formulated fluid. Detailed descriptions of these two processes are summarized below:

Wet Laid Superabsorbent Fiber Composite:

Superabsorbent fiber of the present invention was suspended in a medium comprising at least 60% alcohol (i.e., ethanol or isopropanol) and at most 40% water. The slurry had a consistency of from about 0.1% to about 5%. The slurry was mechanically mixed by a stirrer and transfer to a standard TAPPI sheet mold. The dimensions of the mold were 8 inches by 8 inches (20.3 cm×20.3 cm). The mold is open on the top so that the slurry can be added into the mold. The mold's bottom is air-tight attached to a screen which only allows solvent to go through. However, separation of fiber and solvent is controlled by a valve which connects a vacuum source to the mold. The liquid medium was drained into the sheet mold to form a wet laid sheet of the superabsorbent fiber.

The formed sheet was blotted using blotter paper (DOMTAR 8 inch×8 inch Blotter Paper having a basis wt. of 250+/−10 g/m$^2$, available from Domtar Industries) on both sides to remove interstitial liquid. Optionally, the wet laid sheet was then subjected to an aqueous alcohol medium having a higher content (60 wt %) of alcohol (ethanol or isopropanol) to reduce water content of the sheet. After this additional exposure, the sheet was further dried by blotting with the blotter paper (an optional vacuum source could also be used) to further remove the interstitial liquid. After each blotting, the wet blotters were removed and replaced with dry blotters. The composite was then couched with heavy weight couch roll (12.5 kg, polished stainless steel roll, 33 cm long with 7.6 cm diameter).

The wet sheet after blotting and couching several times was then air dried (or optionally can be oven dried) to between about 85 wt % solids or greater, such as 88-92 wt % solids. As a result of this treatment, interfiber bonds were formed throughout the composite due to the nature of superabsorbent fiber, as well as the difference in evaporation rate between the alcohol and water. For example, the treatment caused the superabsorbent fibers to swell. The increase in size due to swelling allowed each superabsorbent fiber to contact other superabsorbent fibers around it. In addition, the surfaces of the superabsorbent fibers became sticky due to the treatment. As a result of the treatment, the fibers were, among other things, able to covalently bond to each other.

Air Formed then Wet Treated Superabsorbent Fiber Composite:

Superabsorbent fibers of the present invention were air formed into a sheet using a hand sheet former and then densified to a density of from about 0.1 to 0.3 gram/cm$^3$. A solution comprising about 5 wt % cationic polymer material (KYMENE 577H, available from Hercules, Inc. having a place of business in Wilmington, Del., U.S.A.), 52% ethanol and 43% water was prepared and sprayed onto the surface of the sheet. After spraying, the sheet was dried to between about 88-92 wt % solids using a forced-air oven. This process (i.e., spraying and drying) was repeated until the composite had about 2 wt % KYMENE content. It is noted that the KYMENE imparted a soft skin on the surface of the composite while leaving the interior of the composite substantially unaffected. In this case, the interfiber bonds are substantially formed on the surface of the composite only.

Other Approaches:

The above two approaches achieve a common goal: to enable formation of a certain degree of interfiber bonds between the superabsorbent fibers of the present invention either within the entire absorbent composite, or substantially on a surface portion only of the absorbent composite. The interfiber bonds formed as described above are preformed. As used herein, the term "preformed" means that the bonds are formed before incorporation into an absorbent article. By the same mechanism, in-situ formation of interfiber bonds may also be effective to improve both fluid wicking capability and wet integrity. To achieve such in-situ interfiber bond formation, a suitable chemical (such as a cationic polymer material, for example) can be coated onto the surface of the superabsorbent fiber such that upon wetting by body fluid during the use of the absorbent product, the chemical will be ionized to generate charges which are opposite to the charges generated by the superabsorbent fibers. Therefore, due to ionic interaction between two types of the charges on the surface of superabsorbent fibers, bonds will be formed in-situ upon fluid insult. Since superabsorbent fiber is made of anionic material, cationic materials will be suitable for the surface treatment. Examples of such cationic material include, but are not limited to, polyvinyl amine, polyvinyl imine, polyquarternary ammonium, chitosan and chitosan salt. The benefit of this approach is that improved fluid wicking and wet integrity of the invention can be achieved from an air-formed absorbent composite.

Method of Making the Absorbent Composite:

In some aspects, it is desirable to control the degree of interfiber bonds when producing an absorbent composite of the present invention comprising superabsorbent fiber. Controlling the degree of interfiber bonds can result in achieving desired (i.e., improved) fluid wicking capability and/or wet integrity of the absorbent composite, as compared to composites comprising superabsorbent fibers of the present invention which have not been treated as described herein, or in which interfiber bonding has not been controlled. For example, in some aspects, when the degree of interfiber bonding is too high, the resulting absorbent composite may be very stiff and wicking may be hurt due to too much restriction in fiber swelling capability, as well as too little wicking capillary action generated during swelling.

When the absorbent composite of the present invention is produced utilizing alcohol as described above, the alcohol content tends to be the controlling factor to determine the degree of interfiber bonds formed in the absorbent composite. Thus, when the alcohol content is too low (e.g., below 50 wt %), the superabsorbent fiber can swell significantly and form more bonds compared to when the alcohol content is higher than 50 wt %. In general, the higher the alcohol content is, the less the number of interfiber bonds that will be formed.

Absorbent Articles

Figure 10A:
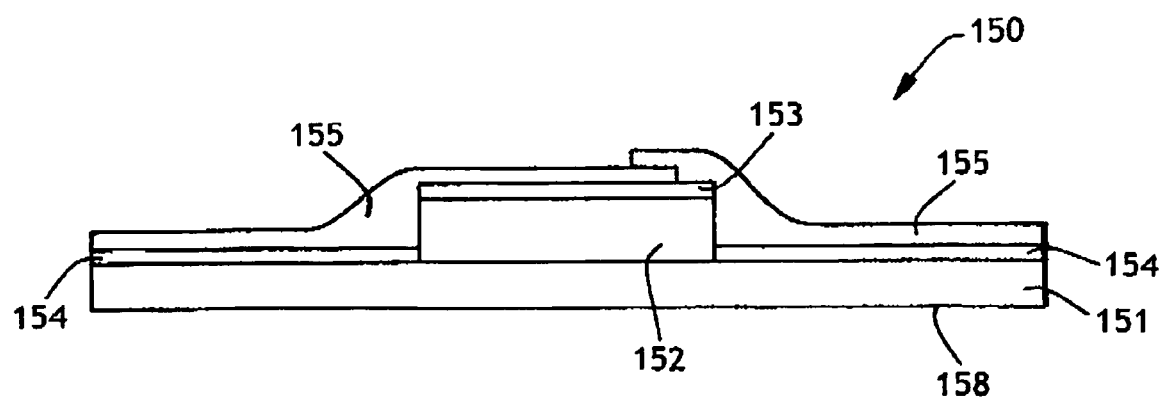
FIG. 10A is a cross-section side view of an absorbent bandage of the present invention.
Figure 10B:
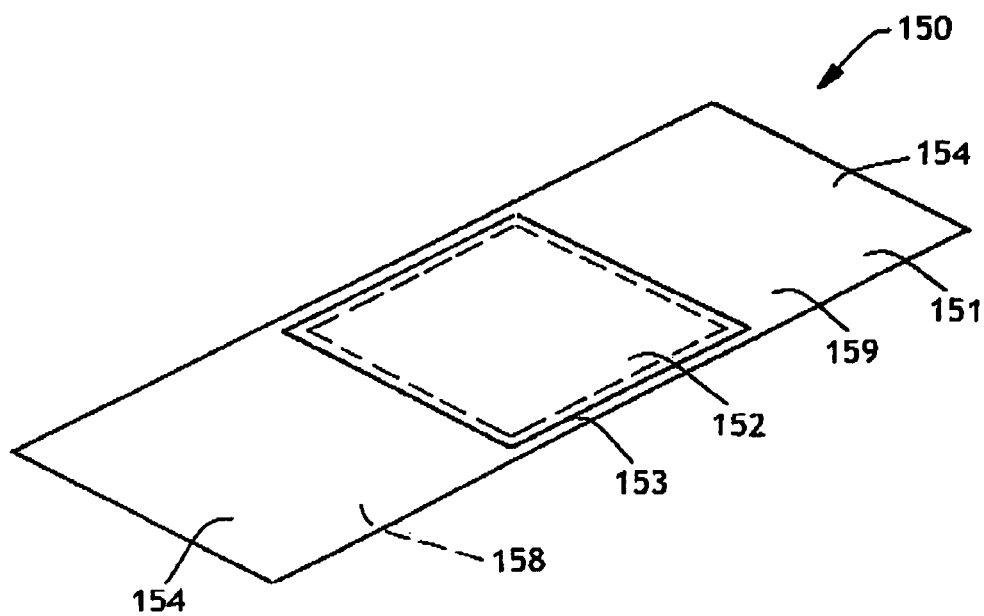
FIG. 10B is a top perspective view of an absorbent bandage of the present invention.

In addition to the absorbent article (in the form of a training pant) described above, in other aspects, the absorbent composite of the present invention may be further exemplified as an absorbent bandage. Attention is directed to FIGS. 10A and 10B, which show a possible configuration for a bandage of the present invention. FIG. 10A shows a cross-section view of the absorbent bandage with optional layers described below. FIG. 10B shows a perspective view of the bandage of the present invention with some of the optional or removable layers not being shown. The absorbent bandage 150 has a strip 151 of material having a body-facing side 159 and a second side 158 which is opposite the body-facing side. The strip is essentially a backsheet and is desirably prepared from the same materials described above for the backsheet. In addition, the strip may be an apertured material, such as an apertured film, or material which is otherwise gas permeable, such as a gas permeable film. The strip 151 supports the absorbent composite 152 of the present invention comprising superabsorbent fibers described herein which is attached to the body facing side 159 of the strip. In addition, an absorbent protective layer 153 may be applied to the absorbent composite 152 and can be coextensive with the strip 151.

The absorbent bandage 150 of the present invention may also have a pressure sensitive adhesive 154 applied to the body-facing side 159 of the strip 151. Any pressure sensitive adhesive may be used, provided that the pressure sensitive adhesive does not irritate the skin of the user. Suitably, the pressure sensitive adhesive is a conventional pressure sensitive adhesive which is currently used on similar conventional bandages. This pressure sensitive adhesive is desirably not placed on the absorbent composite 152 or on the absorbent protective layer 153 in the area of the absorbent composite 152. If the absorbent protective layer is coextensive with the strip 151, then the adhesive may be applied to areas of the absorbent protective layer 153 where the absorbent composite 152 is not located. By having the pressure sensitive adhesive on the strip 151, the bandage is allowed to be secured to the skin of a user in need of the bandage. To protect the pressure sensitive adhesive and the absorbent, a release strip 155 can be placed on the body facing side 159 of the bandage. The release liner may be removably secured to the article attachment adhesive and serves to prevent premature contamination of the adhesive before the absorbent article is secured to, for example, the skin. The release liner may be placed on the body facing side of the bandage in a single piece (not shown) or in multiple pieces, as is shown in FIG. 10A.

In a further aspect, the absorbent composite of the bandage may be placed between a folded strip. If this method is used to form the bandage, the strip is suitably fluid permeable.

Figure 11:
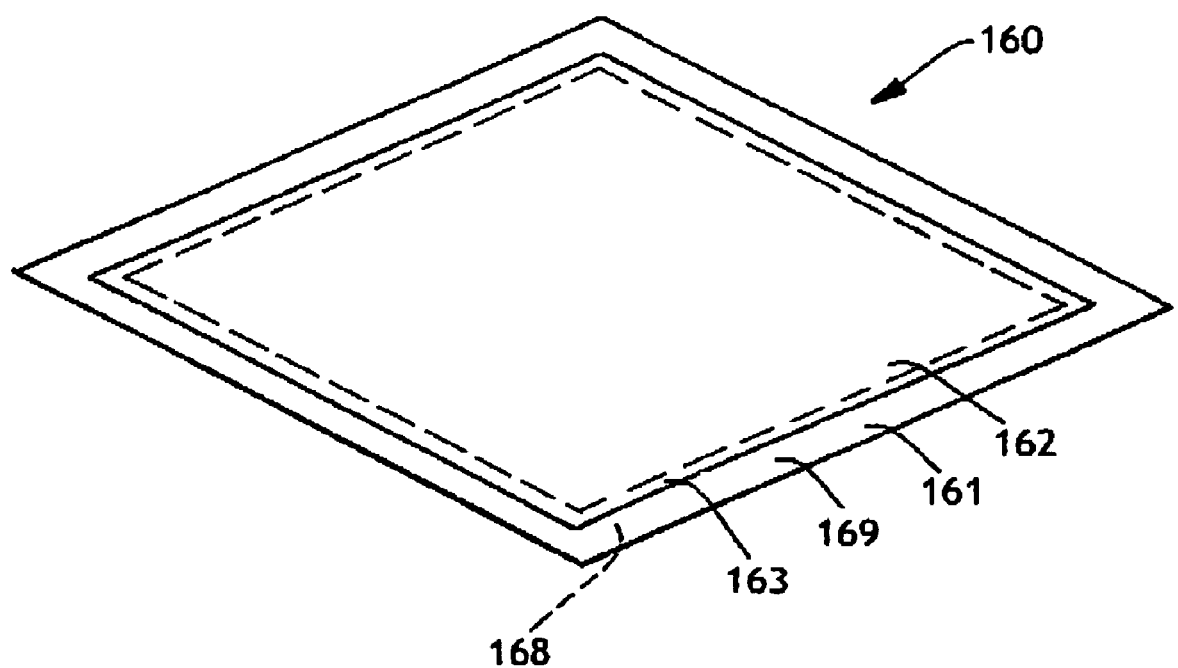
FIG. 11 is a top perspective view of an absorbent bed or furniture liner of the present invention.

In other aspects, absorbent furniture and/or bed pads or liners are also included within the present invention. As is shown in FIG. 11, a furniture or bed pad or liner 160 (hereinafter referred to as a "pad") is shown in perspective. The pad 160 has a fluid impermeable backsheet 161 having a furniture-facing side or surface 168 and an upward facing side or surface 169 which is opposite the furniture-facing side or surface 168. The fluid impermeable backsheet 161 supports the absorbent composite 162 of the present invention which comprises superabsorbent fibers described herein and which is attached to the upward facing side 169 of the fluid impermeable backsheet. In addition, an optional absorbent protective layer 163 may be applied to the absorbent composite. The optional substrate layer of the absorbent composite can be the fluid impermeable layer 161 or the absorbent protective layer 163 of the pad.

To hold the pad in place, the furniture-facing side 168 of the pad may contain a pressure sensitive adhesive, a high friction coating or other suitable material which will aid in keeping the pad in place during use. The pad of the present invention can be used in a wide variety of applications including placement on chairs, sofas, beds, car seats and the like to absorb any fluid which may come into contact with the pad.

Figure 12:
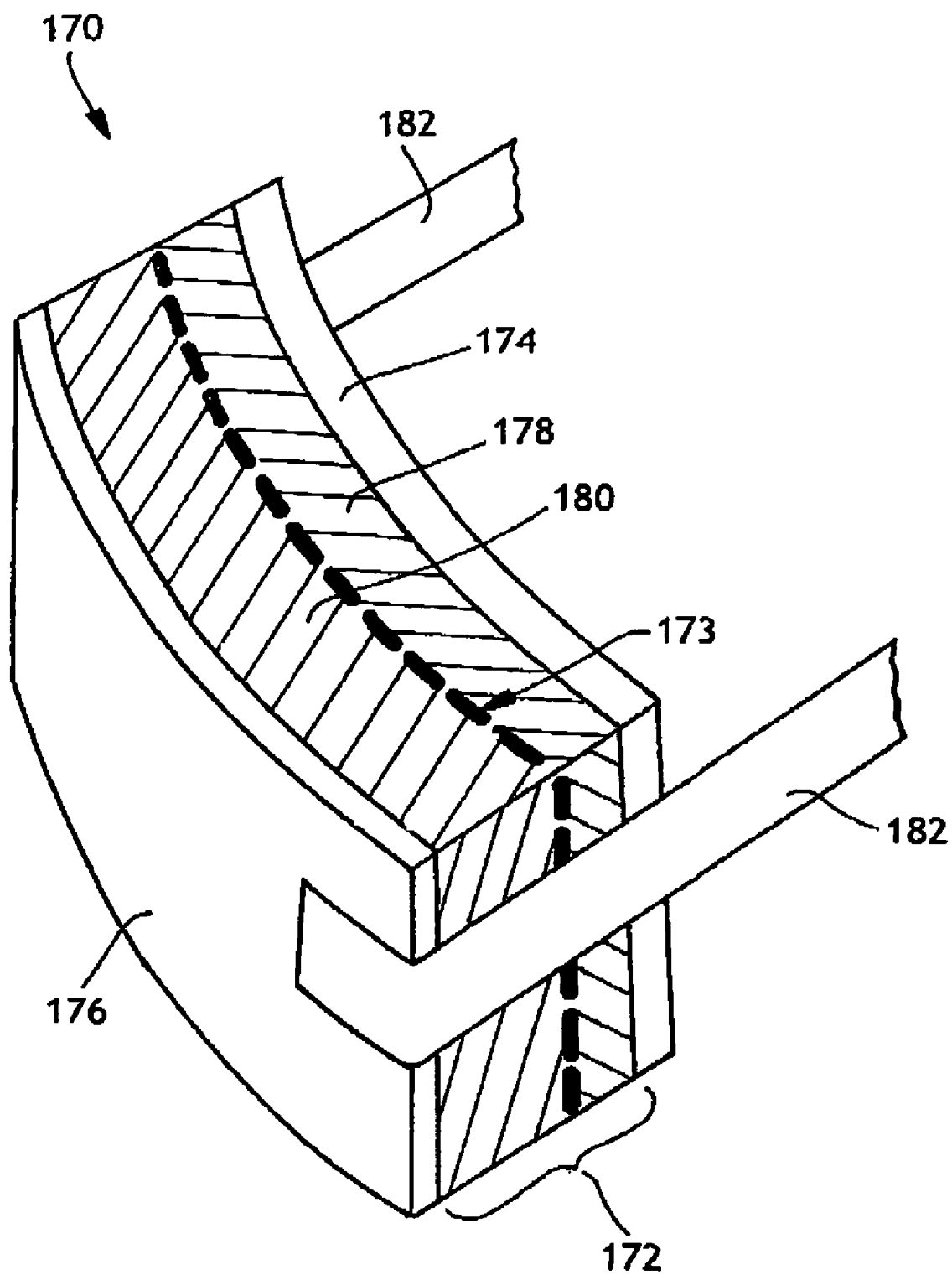
FIG. 12 is a perspective view of an absorbent sweatband of the present invention.

In still other aspects, sports or construction accessories, such as an absorbent headband for absorbing perspiration or drying off equipment are also included within the present invention. As is shown in FIG. 12, a highly absorbent sweatband 170 is shown in perspective. The sweatband 170 has an absorbent composite 172 of the present invention disposed between an optional topsheet 174 and/or an optional fluid impervious backsheet 176. The absorbent composite 172 comprises superabsorbent fibers described herein, and in some aspects can have a low capacity region 178 and a high capacity region 180, and could include an optional additional region (not shown) if desired. The regions could be laminated, as shown by broken line 173. The low capacity region 178 can be positioned towards the user's skin and can maintain a comfortable feel to the user. VELCRO or other fastening device 182 can be used to facilitate adjustment or comfort.

The present invention may be better understood with reference to the following examples.

EXAMPLES

Carboxyalkyl Cellulose Fiber Pad Preparation

Unless otherwise stated, pads comprising the fibers of the present invention were prepared on an airlaid handsheet former, followed by a densification step, such as with a carver press or a nip roller. The resulting pads had a basis weight of approximately 500 gsm and a density of approximately 0.25 g/cc.

Example 1

The Preparation of Pre-Crosslinked Pulp

In this example, the preparation of crosslinked cellulosic pulp is described. The crosslinked cellulosic pulp can be used to make the carboxyalkyl cellulose fibers of the invention.

120 grams of never-dried northern kraft spruce (NKS) pulp (oven-dried (OD) weight is 40 grams) (available from Weyerhaeuser Company) is mixed in a plastic bag with sodium hydroxide and, if necessary, water for 10 minutes at 10% consistency. Liquid is then pressed from the pulp and collected. Crosslinking agent was added to the liquid and then mixed with pulp in the bag. The bag was heated at 85° C. in a water bath for 70 minutes. After reaction, the reacting mixture was diluted with deionized (DI) water, filtered, and repeated to obtain >25% consistency pre-crosslinked pulp for used for carboxymethyl cellulose (CMC) preparation.

Table 1 summarizes suitable crosslinking agents useful in making carboxyalkyl cellulose from crosslinked pulp.

TABLE 1

The preparation of crosslinked pulp useful for making carboxymethyl cellulose fibers.

| Sample | Water g | 10% NaOH g | Crosslinking agent | DS |
|---|---|---|---|---|
| Control | 280 | 0 | 0 | 0.94 |
| 1-1 | 280 | 8 | 8 g 10% DCP | 0.94 |
| 1-2 | 270 | 8 | 2 g 10% glycerol diglycidal | 0.94 |
| 1-3 | 270 | 8 | 2 g 10% PEGDE | 0.91 |
| 1-4 | 270 | 8 | 4 g 10% 1.4 butanediol diglycidal | 0.94 |
| 1-5 | 270 | 0 | 8 g 10% GA and 2 g 10% AS | 0.91 |

DS: degree of carboxyl group substitution
DCP: 1,3-dichloro-2-propanol.
PEGDE: poly(ethylene glycol diglycidal ether).
GA: glyoxal.
AS: aluminum sulfate ($Al_2(SO_4)_3 \cdot 18H_2O$).

Example 2

Morphology of the Representative Crosslinked Carboxymethyl Cellulose Fibers

In this example, the morphology (e.g., twists) of representative crosslinked carboxyalkyl cellulose fibers of the invention is described.

The twists per millimeter were counted for the pulp or fiber samples in their dry condition and in wet condition in a seventy percent ethanol/water solution. The sample fibers were distributed on a microscope slide and the twist count per millimeter was performed by measuring the length of one hundred fibers and counting the number of twists on those fibers. A separate count of fibers with no twists was kept for computing the percent yield. The image analysis system was calibrated using a two millimeter American Optical scale mounted in glass on a microscope slide.

Twist nodes per millimeter=total number of twists/sum of the lengths. %Yield=$100*(1-(Tn/(Tn+100)))$ where Tn is the number of fibers without twists.

TABLE 2

Representative crosslinked carboxymethyl cellulose fiber morphology.

| | Twist per mm | | % Yield | |
|---|---|---|---|---|
| Sample | Dry | Wet | Dry | Wet |
| NKS Pulp | 3.00 | 2.08 | 96.15 | 85.47 |
| 2-1 | 3.81 | 2.58 | 72.46 | 53.76 |
| 2-2 | 5.35 | 2.66 | 85.47 | 60.98 |
| 2-3 | 4.19 | 2.65 | 76.34 | 59.52 |
| 2-4 | 3.18 | 2.68 | 79.37 | 53.48 |
| 2-5 | 3.01 | 2.16 | 68.97 | 60.61 |
| Average | 3.91 | 2.55 | 76.52 | 57.67 |
| Pilot crosslinked CMC fibers | 2.48 | 2.75 | 64.10 | 46.51 |
| Laboratory CMC fibers | 5.62 | 2.35 | 85.47 | 59.17 |

The crosslinked carboxymethyl fibers of the invention had higher twist counts than the starting pulp at dry or wet state. These fibers also had higher twist counts than starting carboxymethyl cellulose fibers when wet, but lower twist counts than the starting carboxymethyl cellulose fibers. The crosslinked carboxymethyl fibers of the invention maintained their twist when wet, while carboxymethyl cellulose fibers without crosslinking lose their twist counts. The crosslinked carboxymethyl fibers of the invention prepared by the pilot run (Pilot crosslinked CMC fibers) have lower dry twist count than starting pulp, the crosslinked carboxymethyl fibers of the invention prepared by laboratory methods, or the starting carboxymethyl cellulose fibers, but higher wet twist count than the starting pulp, the crosslinked CMC from lab, CMC, and lab CMC.

Example 3

The Preparation of Representative CrosslinkedCarboxymethyl Cellulose Fibers and Pads Including the Fibers In this example, the preparation of representative crosslinked carboxymethyl cellulose fibers of the invention and pads including the fibers are described. 409 grams of never-dried carboxymethyl cellulose fibers from high alpha sulfite pulp Olympic HV (the carboxymethyl cellulose fibers were neutralized in 70/30 ethanol/water, filtered and washed with 70/30 ethanol/water, filtered, then washed with 100% ethanol and filtered to 409 grams) (oven dried 70 grams) was mixed in a solution containing 515 grams of ethanol, 960 grams of water, 53.6 grams AA or aluminum acetate dibasic/boric acid (boric acid as stabilizer, 33 percent by weight), and 4.0 grams of Sunrez 747 (a permanent crosslinker) for one hour. After the reaction, the slurry was filtered to obtain 240 grams of wet sample. The sample was pin mill fluffed to obtain fiber bundles. Part of the wet fiber bundles was oven dried at about 60° C. for one hour to obtain dry product fiber bundles (Sample 3-4 and 3-6). The same procedure was used for the same carboxymethyl cellulose fibers with only 50% of aluminum acetate/boric acid used (Sample 3-5 and 3-7). The fibers were tested for aluminum (Al), and boron (B), and the pads from the fibers bundles were tested by FIFE. Control pads with commercial SAP and fluff (CF 416 or NB416) were made for FIFE test for comparison. All wet pads were tested for pad integrity. Pads 3-6 and 3-7 were made with a pad former.

Table 3 summarizes the absorbent properties of representative crosslinked carboxyalkyl cellulose fibers and pads made from the fibers, and fiber metal content.

Example 4

Representative Crosslinked Carboxyalkyl Cellulose Fibers: Aluminum Subacetate

This example describes the treatment of carboxymethyl cellulose fibers with aluminum subacetate, an aluminum crosslinking agent prepared immediately prior to use, to provide crosslinked carboxyalkyl cellulose fibers. This example describes a method for crosslinking carboxyalkyl cellulose fibers with this aluminum crosslinking agent.

7.9 gram of aluminum sulfate hexadecahydrate was dissolved in 69.3 grams of water and 7 grams of calcium carbonate was added slowly with stirring. After completion of $CO_2$ evolution, 16 grams of acetic acid was added slowly with stirring until $CO_2$ release is complete. The mixture was stirred and set for overnight to form a clear solution over a white precipitate. The top layer solution was collected through filtration to obtain 67 grams of clear liquid with a pH of 4.2. Into the liquid, 86 grams of ethanol was added and another 14 grams of water was added. The final solution (MA) had a pH of 5.25. 16.5 gram of solution MA was mixed with 15 grams of ethanol/water (6/4 wt) solution in a spray bottle and the solution was sprayed evenly on 27 grams of never dried cotton linter carboxymethyl cellulose fibers with DS of 0.95 in a plastic bag (OD weight CMC is 10 grams). The carboxymethyl cellulose fibers with solution MA was mixed by hand for half an hour and then dried in a aluminum tray at 66° C. for one hour. The dried product fibers had 4000 ppm of aluminum, and no detectable boron.

The solution MA had 1800 ppm of aluminum and no boron and an IR spectrum different from aluminum acetate stabilized with boric acid or aluminum acetate basic.

Example 5

Representative Crosslinked Carboxyalkyl Cellulose Fibers: Aluminum Monoacetate

This example describes the treatment of carboxymethyl cellulose fibers with aluminum subacetate, an aluminum crosslinking agent prepared immediately prior to use, to provide crosslinked carboxyalkyl cellulose fibers. This example describes a method for crosslinking carboxyalkyl cellulose fibers with this aluminum crosslinking agent.

Solution, Reagent and Admixture Preparations

The aluminum acetate solution used in this process was prepared by modification of the process described in United

TABLE 3

Crosslinked carboxymethyl cellulose fibers and pad properties.

| Sample | AA | Free Swell (g/g) | CRC (g/g) | FIFE insult time (seconds) | | | | Wet Pad Strength | Al/B (ppm) |
|---|---|---|---|---|---|---|---|---|---|
| | | | | T1 | T2 | T3 | T4 | | |
| 3-4 | 100% | 60 | 17 | 18 | 29 | 25 | 24 | strong | 10700/1700 |
| 3-5 | 50% | 50 | 20 | 90 | 70 | 67 | 58 | 3.4 N | 7800/1100 |
| 3-6 | 100% | 60 | 17 | 16 | 48 | 59 | 75 | medium | 10700/1700 |
| 3-7 | 50% | 50 | 20 | 180 | 83 | 180 | 200 | 2.6 N | 7800/1100 |

States Pharmacopoeia (26 p 93) for aluminum subacetate topical solution, described as the diacetate, $Al(O_2CCH_3)_2OH$. In contrast, the solution described herein is for a solution described as the monoacetate, $Al(O_2CCH_3)(OH)_2$.

Aluminum acetate solution was prepared as follows: Aluminum sulfate octadecahydrate (490 g) is dissolved in cold water (560 g, 1-10° C.). Calcium carbonate (244 g) is added in portions with mixing until a stiff slurry is formed. The slurry is diluted with 113 g cold water and any remaining $CaCO_3$ is added. Glacial acetic acid (256 mL) is added with stirring. The mixture is kept cold for 1-2 hours and then filtered under vacuum to give approximately 820 g solution (d=1.0996 g/mL at 20° C.). The concentration of aluminum acetate, dibasic in the solution is 23.4% (w/w). Other solutions of lower concentrations may be produced from this solution by weight/weight serial dilution. The salt solution is unstable to heat and must be kept cold. The best results are obtained if the solution is used within 4 hours.

The following is a balanced chemical reaction for the basic chemistry involved in making aluminum acetate solution:

$$Al_2(SO_4)_3 + 2CH_3CO_2H + 3CaCO_3 + H_2O \rightarrow 2Al(CH_3CO_2)(OH)_2 + 3CaSO_4 + 3CO_2$$

The chemical reaction above is illustrative only, as the recipe uses more than three-times the equivalent amount of acetic acid called for by the stoichiometry given.

Reagents made from aluminum acetate solution are produced as follows:

Reagent 1: Concentrated (23.4% w/w) aluminum acetate, dibasic solution (226 g) is diluted with methanol (620 g) and denatured alcohol (250 g) to afford a reagent containing 4.8% aluminum acetate, dibasic.

Reagent 2: Diluted (14% w/w) aluminum acetate, dibasic solution (247 g) is diluted with methanol (832 g) and denatured alcohol (325 g) to afford a reagent containing 2.5% aluminum acetate, dibasic.

Admixtures of the carboxymethyl cellulose fibers and aluminum salts are produced as follows:

Example 5A

Three samples of carboxymethyl cellulose fibers prepared from NKS pulp (DS about 0.9-1.0) (available from Weyerhaeuser Company) in denatured alcohol (13 g fibers and 53 g alcohol) were treated separately with 260-320 g of Reagent 1 in a container sized such that the fibers were completely immersed in the reagent. The mixtures were covered and allowed to stand with occasional stirring for 1 hour. The samples were suction filtered to give a series of samples with varying retention ratios (R) of 5, 4 and 3, where R=(total wet weight/(fibers-dry weight). The samples were partially dried in a convection oven equipped with an induced draft for 10-20 minutes at 66-68° C. The samples were then pin-milled and returned to the oven for another 60-80 minutes.

Example 5B

Three samples of carboxymethyl cellulose fibers in denatured alcohol, each containing 15 g fibers and 62 g alcohol, are treated separately with 280-350 g of Reagent 2 in a container sized such that the fibers were completely immersed in the reagent. The samples are worked up in identical fashion to those in Example 5A.

Example 6

The Preparation of Representative Crosslinked Carboxymethyl Cellulose Fibers from Crosslinked Cellulose Fibers In this example, the preparation of representative crosslinked carboxymethyl cellulose fibers of the invention were prepared by crosslinking carboxymethyl cellulose prepared from crosslinked cellulose.

The following examples describe the use of crosslinked pulp as a starting material for making carboxyalkyl cellulose (e.g., CMC) that is then further crosslinked (non-permanent crosslinks) to provide superabsorbent carboxyalkyl cellulose. The crosslinked pulp useful in making superabsorbent carboxyalkyl cellulose is crosslinked with a crosslinking agent that provides crosslinks that are stable to the alkaline conditions of the carboxyalkylation reaction. Suitable crosslinking agents include those that form ether crosslinks. Representative crosslinking agents that form ether crosslinks include 1,3-dichloro-2-propanol (DCP), divinyl sulfone (DVS), glycerol diglycidal, 1,4-butanediol diglycidal, and poly(ethylene glycol diglycidal ether) (PEGDE).

Example 6A

The Preparation of Crosslinked Carboxymethyl Cellulose from 1,3-Dichloro-2-propanol Crosslinked Cellulose In this example, the preparation of crosslinked carboxymethyl cellulose from carboxymethyl cellulose prepared from crosslinked pulp (1,3-dichloro-2-propanol crosslinked pulp) is described. In this method, carboxymethyl cellulose prepared from crosslinked pulp is crosslinked with aluminum acetate.

10 grams of air-dried CMC (DS 0.95) from never-dried crosslinked pulp (1,3-dichloro-2-propanol crosslinked pulp, Sample 1-1 in Example 1) was immersed in 100 grams of 75/25 ethanol/water solution with 3% aluminum acetate (dibasic, stabilized with boric acid) for 50 minutes. The slurry was filtered to a weight of 40 grams. The wet samples were then oven dried at 76° C. for 50 minutes (Sample 6A-1).

The same procedure was followed for a low DS CMC (DS 0.8) from a low consistency procedure (Sample 6A-2) and a low DS CMC sample (DS 0.6) from a high consistency procedure (Quantum mixer) (Sample 6A-3) (both control CMCs are from never-dried Prince Albert pulp (available from Weyerhaeuser Company) without pre-crosslinking).

Table 4 summarizes the absorbent properties and metal contents of the product crosslinked carboxyalkyl celluloses.

TABLE 4

Representative crosslinked carboxymethyl cellulose fiber properties.

| Sample | Free swell (g/g) | CRC (g/g) | AUL (g/g) | Al ppm | B ppm |
|---|---|---|---|---|---|
| 6A-1 | 58 | 29 | 40 | — | — |
| 6A-2 | 46 | 26 | 29 | — | — |
| 6A-3 | 52 | 17 | 32 | 11350 | 1570 |

Example 6B

The Preparation of Crosslinked Carboxymethyl Cellulose from Glycerol Diglycidal Crosslinked Pulp In this example, the preparation of crosslinked carboxymethyl cellulose from carboxymethyl cellulose prepared from crosslinked pulp (glycerol diglycidal crosslinked pulp) is described. In this method, carboxymethyl cellulose prepared from crosslinked pulp is crosslinked with aluminum acetate.

15 grams of air-dried CMC (DS 0.95) from never-dried crosslinked pulp (glycerol diglycidal crosslinked pulp, Sample 1-2 in Example 1) was immersed in 330 grams of 50/50 ethanol/water solution with 1.5% aluminum acetate (dibasic, stabilized with boric acid) for 50 minutes. The slurry was filtered to a weight of 60 grams. The wet sample was then oven dried at 76° C. for 50 minutes (Sample 6B-1, pH 6.1). The same procedure was applied to CMC with slurry pH adjustment (using NaOH) to provide Sample 6B-2 (pH 6.9) and Sample 6B-3 (pH 7.7).

Table 5 summarizes the absorbent properties and metal contents of the product crosslinked carboxyalkyl celluloses.

TABLE 5

Representative crosslinked carboxymethyl cellulose fiber properties

| Sample | Free Swell (g/g) | CRC (g/g) |
|---|---|---|
| 6B-1 | 54 | 12 |
| 6B-2 | 54 | 13 |
| 6B-3 | 49 | 22 |

Example 7

The Preparation of Representative Crosslinked Carboxymethyl Cellulose Fibers: Crosslinking with 1,3-Dichloro-2-propanol During Carboxyalkylation and Crosslinking with Aluminum Chloride Post-Carboxyalkylation This example describes the preparation of representative crosslinked carboxymethyl cellulose fibers of the invention that are prepared by two-stage crosslinking: (1) permanent crosslink formation using 1,3-dichloropropanol during carboxyalkylation and (2) non-permanent crosslink formation using aluminum chloride post-carboxyalkylation.

This example compares the absorbent properties of two representative crosslinked carboxyalkyl cellulose fibers of the invention: (1) crosslinked carboxyalkyl cellulose fibers that include non-permanent aluminum crosslinks and (2) crosslinked carboxyalkyl cellulose fibers that include non-permanent aluminum crosslinks and permanent ether crosslinks.

The example also demonstrates the effect of crosslinking agent amount, pulp degree of polymerization (DP), and carboxyalkyl cellulose degree of carboxyl group substitution (DS) on centrifuge retention capacity (CRC).

The first pulp was a lower alpha (86-88%), lower DP (1600-1700 ASTM) kraft fluff pulp designated NB416 manufactured by Weyerhaeuser Company (Pulp A in Table 7).

The second pulp was a high alpha (95%), high DP (2600 ASTM) sulfite dissolving pulp designated Olympic HV manufactured by Weyerhaeuser Company (Pulp B in Table 7).

In the method, the pulp was carboxymethylated with or without addition of 1,3,-dichloro-2-propanol (DCP), a crosslinking agent that provides permanent crosslinks. The crosslinking agent (0, 2, or 4 weight % based on oven-dried pulp) was added together with the monochloro acetic acid during the carboxymethylation process. Two levels of carboxymethylation (DS) were investigated: (1) 0.65-0.75 and (2) 0.95-1.00. After the carboxymethylation reaction was complete, the CMC slurry was neutralized with acetic acid and then washed with ethanol/water mixtures to remove salt. The CMC was washed with 100% ethanol and filtered to a consistency of about 20%

The washed CMC was then crosslinked (e.g., surface crosslinked with an amount of aluminum chloride (a crosslinking agent that provides non-permanent crosslinks)) in an ethanol/water slurry. The consistency of the slurry was about 5% and typically contains 60% ethanol and 40% water. The treated CMC was allowed to soak with the aluminum chloride for about 1 hour and filtered.

The product crosslinked carboxymethyl cellulose was dried in a forced-air oven at about 65° C. until partially dried and then removed and treated in a pin-fluffer to minimize clumpiness. In general, the pin-fluffer has a motor-driven rotating shaft centered in a tapered hopper. There are pins attached perpendicularly to the shaft near the bottom of the hopper, close to where the material being fluffed exits. As the material is fed into the hopper, it falls on the rotating pins where it is partially fiberized before it falls into the collection bin under the fluffer. The crosslinked carboxymethyl cellulose was then returned to the oven to complete the drying.

Once dry, the crosslinked carboxymethyl cellulose may be optionally heat treated at higher temperatures to -increase the amount of crosslinking.

Absorbent capacity (CRC) generally decreased with increasing levels of permanent crosslinking and aluminum chloride treatment. As permanent crosslinking levels were increased, less aluminum chloride treatment was required to achieve a given CRC.

With Pulp A, the amount of CRC lost as the permanent crosslinking level is increased is minimal. A 4% permanent crosslinking level appears best for Pulp A. CRC decreases more rapidly with increased permanent crosslinking for Pulp B; a 2% permanent crosslinking level appears best.

CRC decreases with DS. CRC values are generally below 20 g/g for Pulp A at 0.75 DS. CRC values for Pulp B are also lower at 0.75 DS than at 0.95 DS, but remain above 20 g/g for lower aluminum chloride levels.

At low levels of permanent crosslinking and/or DS, Pulp B (higher DP and alpha pulp) has greater capacity levels than Pulp A (lower DP and alpha pulp). At higher levels of permanent crosslinking and high DS, Pulp A tends to have higher capacity.

The composition and absorbent properties (CRC) of representative crosslinked carboxyalkyl cellulose fibers of the invention are summarized in Table 7.

The following examples describe the preparation of representative crosslinked carboxyalkyl cellulose fibers of the invention.

Example 7A

The Addition of a Permanent Crosslinking Agent During the Preparation of Carboxymethyl Cellulose from Never-Dried Kraft Pulp This example describes the preparation of carboxymethyl cellulose fibers by permanent crosslink formation using 1,3-dichloropropanol during carboxyalkylation. Never-dried kraft pulp (200.0 g, oven dried NB416) was mixed with isopropanol (11.36 L) under nitrogen environment at about 20-22° C. for 30 min. A sodium hydroxide solution (167.25 g in water with a total weight of 620.15 g) was added dropwise over 30 minutes and the reaction was left to stir for 1 h. A solution of monochloroacetic acid (181.50 g) and 1,3,-dichloro-2-propanol (8.0 g) in isopropanol (445 ml) was added dropwise to the stirring pulp over 30 min while the reaction temperature was increased to 55° C. The reaction was stirred for 3 h and then filtered, the filtered product was placed in 12 L 70/30 methanol/water solution, and neutralized with acetic acid. The resulting slurry was collected by filtration, washed one time each with 12 L 70/30, 80/20, and 90/10 ethanol/water solutions and then finally with 100% methanol or ethanol to provide the product crosslinked carboxymethyl cellulose (Sample 7A).

Example 7B

The Preparation of Carboxymethyl Cellulose from Never-Dried Kraft Pulp

This example describes the preparation of representative crosslinked carboxymethyl cellulose fibers of the invention that are prepared by non-permanent crosslink formation using aluminum chloride post-carboxyalkylation.

An aluminum chloride crosslinking solution was prepared by combining 143.9 g of 100% denatured ethanol, 131.93 grams of water and 0.408 g of aluminum chloride hexahydrate. To this solution were added 69.00 g of ethanol wet (21.74% solids) carboxymethylcellulose (prepared as described in Example 1). Based on these proportions, the active aluminum chloride applied to the CMC fiber was 1.5% and the ratio of ethanol to was 60% to 40%. The mixture of CMC fiber and crosslinking agent solution was mixed and then allowed to stand at room temperature for 1 hour. After standing the slurry was filtered to a weight 60.59 g. and then oven dried at 68° C. Mid-way through the drying the sample was pin-fluffed to minimize clumping and then returned to the oven until dry to provide crosslinked carboxymethyl cellulose fiber (Sample 7B).

Example 7C

The Addition of a Permanent Crosslinking Agent During the Preparation of Carboxymethyl Cellulose from Never-Dried Kraft Pulp This example describes the preparation of representative crosslinked carboxymethyl cellulose fibers of the invention that are prepared by two-stage crosslinking: (1) permanent crosslink formation using 1,3-dichloropropanol during carboxyalkylation and (2) non-permanent crosslink formation using aluminum chloride post-carboxyalkylation.

An aluminum chloride crosslinking solution was prepared by combining 150.08 g of 100% denatured ethanol, 131.93 grams of water and 0.489 g of aluminum chloride hexahydrate. To this solution were added 62.81 g of ethanol wet (23.88% solids) carboxymethylcellulose (Sample 7A, prepared as described in Example 7A). Based on these proportions, the active aluminum chloride applied to the CMC fiber was 1.8% and the ratio of ethanol to was 60% to 40%. The mixture of CMC fiber and crosslinking agent solution was mixed and then allowed to stand at room temperature for 1 hour. After standing the slurry was filtered to a weight 58.03 g. and then oven dried 68 C. Mid-way through the drying the sample was pin-fluffed to minimize clumping and then returned to the oven until dry to provide a representative crosslinked carboxymethyl cellulose fiber of the invention (Sample 7C).

Table 6 summarizes the absorbent properties (CRC) of representative crosslinked carboxyalkyl cellulose fibers.

TABLE 6

Centrifuge retention capacities for representative crosslinked carboxymethyl cellulose fibers.

| Sample | CRC (g/g) |
| --- | --- |
| 7B | 29.0 |
| 7C | 21.9 |

TABLE 7

Representative crosslinked carboxymethyl cellulose composition and centrifuge retention capacity.

| Sample | $AlCl_3$ (wgt % wgt CMC) | Pulp | CMC DS | DCP (wgt % wgt CMC) | CRC (g/g) |
| --- | --- | --- | --- | --- | --- |
| 7-1 | 1.5% | A | 0.95 | 0% | 29.0 |
| 7-2 | 2.8% | A | 0.95 | 0% | 18.0 |
| 7-3 | 5.0% | A | 0.95 | 0% | 12.0 |
| 7-4 | 0.8% | A | 1.01 | 2% | 31.0 |
| 7-5 | 1.5% | A | 1.01 | 2% | 26.1 |
| 7-6 | 2.5% | A | 1.01 | 2% | 21.2 |
| 7-7 | 0.5% | A | 1.00 | 4% | 30.4 |
| 7-8 | 1.0% | A | 1.00 | 4% | 27.3 |
| 7-9 | 1.8% | A | 1.00 | 4% | 21.9 |
| 7-10 | 1.0% | B | 0.99 | 0% | 23.0 |
| 7-11 | 2.0% | B | 0.99 | 0% | 36.5 |
| 7-12 | 4.0% | B | 0.99 | 0% | 24.1 |
| 7-13 | 0.5% | B | 0.98 | 2% | 36.6 |
| 7-14 | 1.3% | B | 0.98 | 2% | 24.7 |
| 7-15 | 2.0% | B | 0.98 | 2% | 18.4 |
| 7-16 | 0.4% | B | 0.99 | 4% | 19.2 |
| 7-17 | 0.8% | B | 0.99 | 4% | 19.9 |
| 7-18 | 1.5% | B | 0.99 | 4% | 16.5 |
| 7-19 | 1.0% | A | 0.72 | 0% | 20.3 |
| 7-20 | 2.0% | A | 0.72 | 0% | 16.7 |
| 7-21 | 4.0% | A | 0.72 | 0% | 11.6 |
| 7-22 | 0.5% | A | 0.68 | 2% | 17.9 |
| 7-23 | 1.3% | A | 0.68 | 2% | 16.1 |
| 7-24 | 2.0% | A | 0.68 | 2% | 14.4 |
| 7-25 | 0.4% | A | 0.71 | 4% | 14.2 |
| 7-26 | 0.8% | A | 0.71 | 4% | 13.2 |
| 7-27 | 1.5% | A | 0.71 | 4% | 12.3 |
| 7-28 | 0.8% | B | 0.68 | 0% | 37.5 |
| 7-29 | 1.8% | B | 0.68 | 0% | 31.2 |
| 7-30 | 3.8% | B | 0.68 | 0% | 17.3 |
| 7-31 | 0.5% | B | 0.69 | 2% | 22.3 |
| 7-32 | 1.0% | B | 0.69 | 2% | 20.2 |
| 7-33 | 1.5% | B | 0.69 | 2% | 18.7 |
| 7-34 | 0.3% | B | — | 4% | 14.6 |
| 7-35 | 0.6% | B | — | 4% | 14.0 |
| 7-36 | 1.2% | B | — | 4% | 13.0 |

Example 8

The Olympic HV wood pulp (200 g oven dried basis) was mixed with isopropanol (11.36 L) under nitrogen environment at about 20-22° C. for 30 min. A solution of sodium hydroxide and water was added dropwise over 30 minutes and the reaction was left to stir for 1 h. The amount of sodium hydroxide was adjusted depending on the amount of monochloroacetic acid and DCP that was used in order to provide sufficient sodium hydroxide to react with all carboxyl and halogen functional groups. The amount of water was adjusted to maintain constant water to cellulose ratio. The amounts of DCP, sodium hydroxide, MCAA, crosslinking agents and water are summarized in Table 8.

A solution of monochloroacetic acid and DCP in isopropanol (Ratio of IPA to MCAA=1.91 g/g) was added dropwise to the stirring pulp over 30 min while the reaction temperature was increased to 55° C. The reaction was stirred for 3 h and then filtered, the filtered product was placed in 12 L 70/30 ethanol/water solution, and neutralized to a pH between 6.8 and 7.0 with acetic acid. The resulting slurry was collected by filtration, washed one time each with 12 L 70/30, 80/20, and 90/10 ethanol/water solutions and then finally with 100% methanol or ethanol and allowed to air dry to provide a bulk cross-linked carboxyalkyl wood pulp fiber.

Examples 8-1 to 8-3

The never dried carboxyalkyl cellulose fiber was added to a solution (Formula 25) containing the desired amount of crosslinking agent which is prepared as described below:

The starting carboxymethyl cellulose fiber usually contains a significant amount of ethanol. As in the case below, the carboxymethyl cellulose contains 75% ethanol and 25% CMC by weight. The recipe accounts for the ethanol already associated with the CMC and solvents are adjusted so that the final reaction mixture contains 30-33% ethanol, 48-51% methanol, and 11-14% water. The other ingredients are also adjusted to give a final reaction concentration of 3.4-3.6% CMC; 2.1-2.2% aluminum acetate, dibasic; aluminum sulfate 0.0120-0.0132%; glutaraldehyde 0.023-0.024% and glyoxal 0.061-0.063%. The carboxymethyl cellulose fiber is added to a large reactor and a pre-mixed solution containing all the other ingredients is added. The reaction mixture is stirred occasionally for one (1) hour, and filtered to obtain a wet mass weighing 1200-1400 g. The material is dried at 68° C. until the weight is 600-700 g, then pin-milled, and returned to drying until the mass is 330-350 g, or until no alcohol is detected.

Example 8-4

The never dried carboxylalkyl cellulose fiber was added to a solution containing the desired amount of aluminum chloride dissolved in a 60/40 weight/weight alcohol/water solvent mixture to form a slurry having a consistency of 4.35% (weight basis). The slurry of carboxyalkyl cellulose fiber, surface cross-linker mixed and then allowed to stand at room temperature for 1 hour. After standing, the slurry was filtered to a wet weight to dry weight ratios of approximately 4 to 1 and then oven dried at 68° C. Mid-way through the drying the sample was pin-fluffed to minimize clumping and then returned to the oven until dry to provide surface cross-linked carboxyalkyl cellulose fiber Example 9

Absorbent Composite Comprising Superabsorbent Fibers Treated with an Ethanol/Water Solution Bulk Crosslinking and Carboxymethylation:

200.0 g, oven dried weight of never-dried northern Kraft pulp (Prince Albert Softwood, made from mixed softwoods available from Weyerhaeuser Company) was mixed with 11.36 L of isopropanol under a nitrogen environment at about 20-22° C. for 30 min. A sodium hydroxide solution (167.25 g NaOH in water with a total weight of 620.15 g) was then added dropwise over a 30 minute period. The resulting reaction was left to stir for 1 hour.

A solution of 181.50 g monochloroacetic acid and 8.0 g of 1,3,-dichloro-2-propanol in 445 ml of isopropanol was added dropwise to the stirring pulp over 30 min while the reaction temperature was increased to 55° C. The reaction was stirred for 3 hours and then filtered. The filtered product was placed in 12 L of a 70 wt % methanol/30 wt % water solution, and then neutralized with acetic acid. The resulting slurry was collected by filtration, washed one time each with 12 L of 70 wt % ethanol/30 wt % water, 80 wt % ethanol/20 wt % water, and 90 wt % ethanol/10 wt % water solutions and then finally with 100% methanol (or alternatively ethanol) to provide the product crosslinked carboxymethyl cellulose.

Surface Crosslinking:

A surface crosslinking solution was prepared in two steps by first dissolving 61.3 grams of aluminum acetate (basic, stabilized with boric acid) and 0.70 grams of aluminum sulfate octadecahydrate in 348.6 grams of water and then diluting with 586.7 grams of denatured ethanol and 1387.1 grams of methanol. The mixture was further treated with 1.33 grams of 1:1 (w %/w %) glutaraldehyde:water and 4.35 grams of 40% glyoxal (w %/w %) in water. To this solution were added 69.00 g of ethanol wet carboxymethylcellulose (CMC) fluff (21.74% solids) (prepared as described above in this Example). Based on these proportions, the active crosslinking components applied to the CMC fiber was 1.5% and the ratio of ethanol to water was approximately 60 wt % to 40 wt %. It is understood that the optimal alcohol content depends on the superabsorbent fiber. For example, if the fiber has a higher degree of crosslinking, less alcohol will be required, and vice versa.

The mixture of CMC fiber and crosslinking agent solution was mixed with a metal spatula for 10-20 seconds and then allowed to stand at room temperature for 1 hour. Then the slurry was filtered to a weight 60.59 g and then oven dried at 68° C. Approximately half-way through the drying, the sample was pin-fluffed (described above) to minimize clumping and then returned to the oven until dried to between about

TABLE 8

Representative crosslinked carboxymethyl cellulose composition and pad saturation capacity and FIFE intake time.

| | CMC Composition | | | | Surface | Pad Parameter | | Sat. Capacity | FIFE Intake Time (sec) | | |
|---|---|---|---|---|---|---|---|---|---|---|---|
| Sample | DCP | NaOH | $H_2O$ | MCAA | Crosslinker | Basis Wt. | Density | (g/g) | $1^{st}$ Insult | $2^{nd}$ Insult | $3^{rd}$ Insult |
| 8-1 | 0 | 162.3 | 452.9 | 181.5 | Formula 25 | 500 | 0.22 | 18.9 | 11.0 | 16.0 | 14.0 |
| 8-2 | 4 | 164.8 | 452.9 | 181.5 | Formula 25 | 489 | 0.15 | 16.1 | 13.8 | 48.8 | 94.0 |
| 8-3 | 4 | 164.8 | 452.9 | 181.5 | Formula 25 | 509 | 0.18 | 16.1 | 14.0 | 143.7 | 593.0 |
| 8-4 | 4 | 164.8 | 452.9 | 181.5 | 0.5% $AlCl_3$ | 507 | 0.19 | 23.0 | 536.8 | 848.3 | |

88-92 wt % solids to provide bulk and surface crosslinked carboxymethyl cellulose fiber.

Wet Laying and Treatment with Crosslinking Agent:

A 3-Liter Erlenmeyer flask was charged with a mixture of 33.0 grams of fibrous bulk-crosslinked carboxymethylcellulose wetted with 123.3 grams denatured ethanol (as described above in this Example, having 21.1 wt % solids). The wet fiber was diluted with 923 grams of denatured ethanol and 680 grams deionized water to provide a slurry having 1.5 wt % total solids. The slurry was hand-shaken and added to a 20.3 cm×20.3 cm sheet mold equipped with an air-driven stirrer at the center of the mold. The mold was a TAPPI standard sheet mold having dimensions 8 inches by 8 inches (20.3 cm×20.3 cm). It is open on the top so that the slurry can be added into the mold. Its bottom is air-tight attached to a screen which only allows solvent to drain through. However, separation of fiber and solvent is controlled by a valve which connects to a vacuum source. After mixing for 1 minute, the stirrer was quickly removed and the drain was opened to form a composite sheet of carboxymethyl cellulose fiber.

The sheet was placed between two sheets of blotter paper (each blotter weighed 15.5 grams, OD) and submerged in a bath of 100% denatured ethanol for 10 minutes such that ethanol completely covered the sheet and blotter papers. Afterwards the sheet and blotter papers (114.6 grams total) were stripped of excess alcohol by drawing the sheet and blotters over a thin slit (22.9 cm long by 0.3 cm wide) connected to a vacuum (26.5 inches of mercury) to give 76.6 g total weight. The sheet and blotters were returned to a fresh ethanol bath for 10 minutes, and the exchange process was repeated for a total of 3 times to afford a total wet sheet and blotters weight of 74.2 grams.

The exchanged sheet and blotters were then impregnated twice by submerging in the surface crosslinking agent solution described above in this Example (i.e., contains aluminum salt, octadecahydrate, glyoxal, and glutaraldehyde) for 10 minutes such that the surface crosslinking agent solution completely covered the sheet and blotter papers. Afterwards the sheet and blotter papers were stripped of excess surface crosslinking agent by drawing the sheet and blotters over a thin slit (22.9 cm long by 0.3 cm wide) connected to a vacuum (26.5 inches of mercury). The sheet and blotters were returned to a fresh surface crosslinking agent solution bath for 10 minutes, and the exchange process was repeated for a total of 3 times. However, on the final exchange, the impregnated sheets were not vacuumed to afford a sheet-only weight of 131.6 grams. The absorbent composite sheet was removed from the blotter papers, and the sheet was dried in a forced-air oven at 68° C. as needed to 88-92 wt % total solids.

Example 10

Compartive Examples for the Treated Absorbent Composite of Example 9

Three samples were prepared and used as comparative examples (i.e., controls) for the composite of Example 9.

Control 10-1

Control 10-1 was a carboxymethyl cellulose wet laid absorbent composite prepared exactly as Example 9 above, except without using both the bulk crosslinking agent (1,3-dichloro-2-propanol) and the surface crosslinking agent (aluminum salt, glutaraldehyde and glyoxal).

Control 10-2

Control 10-2 is a wood pulp sheet (DOMTAR 8 inch×8 inch Blotter Paper having a basis wt. of 250+/−10 $g/m^2$, available from Domtar Industries).

Control 10-3

Control 10-3 is an absorbent composite containing 60% commercial superabsorbent (SXM 9300, available from Stockhausen Inc.) and 40% wood pulp fluff (NB 416, available from Weyerhaeuser Company).

Control 10-4

Control 10-4 is the composite of Example 9, but without the alcohol/water solution treatment of the composite.

The composite of Example 9 and of the comparative examples (Control 10-1, 10-2, 10-3 and 10-4) were then tested for Wet Integrity, Vertical Wicking Height, and Vertical Wicking Capacity using the Wet Integrity Test and Vertical Wicking Tests described above. The results can be seen below in Table 9 below.

TABLE 9

| Vertical Integrity and Wet Wicking Tests | | | |
|---|---|---|---|
| Sample | Wet Integrity Rank | V. Wicking Height (inch) | V. Wicking Capacity (g/g) |
| Example 9 | 5 | 6.2 | 15.8 |
| Control 10-1 | 0 | 0 | 0 |
| Control 10-2** | N/A | N/A | N/A |
| Control 10-3 | 0 | 2.5 | 7.6 |
| Control 10-4** | N/A | N/A | N/A |

**The wet integrity of this sample was such that when liquid wicked into the sample, the composite fell apart. Therefore, Wet Integrity, Vertical Wicking Height, and Vertical Wicking Capacity measurements could not be obtained.

It can be seen that treatment of the absorbent composite comprising the superabsorbent fibers described herein with an approximately 60 wt % ethanol/40 wt % water solution resulted in a composite having an overall vertical wicking and wet integrity that is superior to the comparative examples.

In addition to the samples described above, several attempts were made to wet lay sheets at various ratios of ethanol to water using the fibrous carboxymethylcellulose obtained from Example 9. In general good sheet formation could only obtained using between about 50 wt % and 70 wt % ethanol for that particular fiber. Higher levels of ethanol (i.e., greater than about 70 wt %) tended to result in poorer formation because the fibers tended to not disperse as well. Thus, these samples did not have a desirable integrity. In contrast, sheets having higher water levels (i.e., less than about 50 wt % alcohol) resulted in sheets that tended to be more stiff and hard. Sheets made in this fashion tended to not fiberize very well, and instead tended to break into flakes, rather than individual fibers. The materials of both of these scenarios described herein (i.e., high alcohol or high water content) were not suitable to be tested by the vertical wicking test due to a lack of integrity or capillary structure.

Example 11

Absorbent Composite Comprising Superabsorbent Fibers Treated with a Cationic Material/Ethanol/Water Solution In this example, absorbent composites comprising bulk/surface crosslinked carboxymethyl cellulose fibers were prepared, similarly to Example 9. The fibers were air formed into twelve air laid composite sheets with a basis weight of 650 gsm, a density of approximately 0.23 g/cc and dimensions of 25.4 cm×43.1 cm.

Control 11-1

Half of the composite sheets (i.e., six) were utilized to cut absorbent composites from the sheets. Two composites (each with a retangular dimension of 90 mm×354 mm) were cut from each of the sheets. Each composite was then prepared into 12 diapers having a topsheet, a backsheet and with the composite disposed between the topsheet and backsheet to function as the absorbent core component. This set of diapers (Code B) was then tested using mannequins as described below.

Example 11-2

The other half of the composite sheets (i.e., the remaining six) were surface treated by spraying a solution containing 5 wt % KYMENE 577H (a cationic polymer material available from Hercules, Inc.), 52 wt % ethanol and 43 wt % water. The composite was dried to about 90 wt % solids and the solution re-applied. This process was continued until a total add-on level of KYMENE of 2 wt % based on total weight of the sheet was achieved. It was noted that the KYMENE was substantially located on the surface portion of the composite, while leaving the interior portion of the sheet substantially free of the KYMENE. The treatment is termed as "Wet Enhancement Treatment" and is intended to enhance fluid wicking capability. Twelve absorbent composites having dimensions of 90 mm×354 mm were then cut from the sheets and then converted into diapers as described in Example 11-2 above. This set of diapers (Code D) was then tested using mannequins as described below.

Control 11-3

This comparative example included diapers that were similar in construction to Control 11-1 and Example 11-2. However, the absorbent core component of the comparative diapers consisted of 41 wt % commercial superabsorbent particles (FAVOR SXM 9300, available from Stockhausen, Inc.) and 59% wood pulp fluff (NB416, available from Wayerhaeuser Company). This set of diapers (Code F) was then tested using mannequins as described below.
Evaluation The three codes of diapers were tested by a mannequin diaper evaluation. Mean Load at Failure information was obtained from the study, and the Diaper Efficiency was calculated using the ratio of mean load at failure to product capacity. Product capacity was measured on the entire diaper product (not just absorbent core).

The dry weight of each diaper was noted prior to testing. For each diaper code, all of the articles were tested in the sitting position with insult liquid added using "female" mannequins. The insult liquid (0.9 wt % aqueous sodium chloride solution) was set at room temperature (~20° C.). The absorbent articles were then each insulted up to four times with 70 ml of the insult liquid for each insult (with a hold time between each insult of 15 minutes) until each product leaked (i.e., once the product began to leak, the insult was stopped, even if less than 70 ml had been added. Also, no further insults were conducted on that particular article once the article leaked). The load at leak was then noted for each product. The products were removed after the leak and weighed. The mean load at failure was determined by subtracting the dry weight from the wet weight, and then determining the mean for each code. In addition, the product capacity was determined for each code using the SAT CAP Test described above, and the diaper efficiency was determined by dividing the mean load at failure by the product capacity. The results can be seen in Table 10 below.

TABLE 10

Diaper Mannequin Study Results

| Diaper Code | Example No. | Mean Load at Failure (g) | Diaper Efficiency |
| --- | --- | --- | --- |
| B | Control 11-1 | 191.61 | 43% |
| D | Example 11-2 | 255.41 | 69% |
| F | Control 11-3 | 256.57 | 61% |

From the results, it is seen that without wet enhancement treatment (i.e., treatment with the cationic material/alcohol/water solution), the absorbent composite (Code B) results in a diaper that exhibits a worse diaper performance than a diaper with a composite of the present invention (Code D) due to a lower absorbent core efficiency caused by lack of fluid wicking capability and integrity. It can also be seen that when the absorbent composite of the present invention is treated in accordance with the present invention, the absorbent composite (Code D) results in a diaper that has a similar performance as a more conventional diaper (Code F), and an improved absorbent core efficiency over the Code F diapers.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent article comprising an absorbent composite;
   wherein the absorbent composite comprises substantially water-insoluble, water-swellable, non-regenerated, carboxyalkyl cellulose fibers;
   wherein the substantially water-insoluble, water-swellable, non-regenerated, carboxyalkyl cellulose fibers have a surface having the appearance of the surface of a cellulose fiber;
   wherein the substantially water-insoluble, water-swellable, non-regenerated, carboxyalkyl cellulose fibers comprise a plurality of first intra-fiber multi-valent metal ion crosslinks and a plurality of second intra-fiber crosslinks selected from ether crosslinks or ester crosslinks; and wherein the absorbent composite has been subjected to a treatment to create inter-fiber bonding.

2. The absorbent article of claim 1 wherein the inter-fiber bonding is present only on the surface of the absorbent composite.

3. The absorbent article of claim 1 wherein the inter-fiber bonding will be formed in-situ upon fluid insult.

4. The absorbent article of claim 1 wherein the treatment is selected from an alcohol/water solution or a cationic polymer/alcohol/water solution.

5. The absorbent article of claim 3 wherein the alcohol is selected from ethanol or isopropanol.

6. The absorbent article of claim 3 wherein the alcohol is present in the solution in an amount between about 50 wt % and 70 wt %.

7. The absorbent article of claim 1 wherein the absorbent composite has been dried to about 88-92 wt % solids prior to the treatment.

8. The absorbent article of claim 1 wherein the absorbent composite comprises from 90 wt % to 100 wt % of the substantially water-insoluble, water-swellable, non-regenerated, carboxyalkyl cellulose fibers.

9. The absorbent article of claim 1 wherein the multi-valent metal ion crosslinks comprise one or more metal ions selected from the group consisting of aluminum, boron, bismuth, titanium, zirconium, cerium, and chromium ions, and mixtures thereof.

10. The absorbent article of claim 1 wherein the second crosslinks are from 1,3-dichloro-2-propanol.

11. The absorbent article of claim 1 wherein the absorbent composite exhibits a vertical fluid wicking distance of at least about 5 inches as measured by the Vertical Wicking Test.

* * * * *